US008956622B2

(12) United States Patent
Bagnard et al.

(10) Patent No.: US 8,956,622 B2
(45) Date of Patent: Feb. 17, 2015

(54) PEPTIDIC ANTAGONISTS OF CLASS III SEMAPHORINS/NEUROPILINS COMPLEXES

(75) Inventors: Dominique Bagnard, Colmar (FR); Lise Roth, Strasbourg (FR); Cécile Nasarre, Strasbourg (FR); Pierre Hubert, Saint-Didier (FR); Sylvie Dirrig-Grosch, Lingolsheim (FR); Gerard Cremel, Lingolsheim (FR); Dominique Aunis, Strasbourg (FR)

(73) Assignee: INSERM—Institut National de la Sante et de la Recherche Medicale, Paris (FR)

( * ) Notice: Subject to any disclaimer, the term of this patent is extended or adjusted under 35 U.S.C. 154(b) by 1480 days.

(21) Appl. No.: 11/993,509

(22) PCT Filed: Jun. 28, 2006

(86) PCT No.: PCT/IB2006/002334
§ 371 (c)(1),
(2), (4) Date: Oct. 20, 2008

(87) PCT Pub. No.: WO2007/000672
PCT Pub. Date: Jan. 4, 2007

(65) Prior Publication Data
US 2010/0222261 A1    Sep. 2, 2010

(30) Foreign Application Priority Data
Jun. 28, 2005 (EP) .................................... 05291392

(51) Int. Cl.
| A61K 38/00 | (2006.01) |
| C07K 7/00 | (2006.01) |
| C07K 14/71 | (2006.01) |
| C07K 14/705 | (2006.01) |

(52) U.S. Cl.
CPC . *C07K 14/71* (2013.01); *C07K 7/00* (2013.01); *A61K 38/00* (2013.01); *C07K 14/70546* (2013.01)
USPC ..................... 424/192.1; 424/185.1; 530/300; 530/326

(58) Field of Classification Search
USPC ......... 530/350, 324, 326, 300; 435/320, 69.1; 424/130, 185.1, 192.1; 514/16.4, 21.4, 514/19.3, 1
See application file for complete search history.

(56) References Cited

U.S. PATENT DOCUMENTS
6,900,288 B1    5/2005 Behl et al.
2003/0105000 A1*    6/2003 Pero et al. ....................... 514/12

FOREIGN PATENT DOCUMENTS
| WO | WO99/04263 | 1/1999 |
| WO | WO 9929858 A1 * | 6/1999 |
| WO | WO 2004/023973 * | 3/2004 |

OTHER PUBLICATIONS

Cohen (Int J Radiat Oncol Biol Phys, 1987, 13:251-8).*
Bowie et al (Science, 1990, 247:1306-1310).*
Skolnick et al. (Tibtech 18:34-39, 2000).*
Ibragimova and Eade (Biophysical Journal, Oct. 1999, vol. 77, pp. 2191-2198).*
Burgess et al (J of Cell Bio. 111:2129-2138, 1990).*
Lazar et al (Molecular and Cellular Biology, 1988, 8:1247-1252).*
Gura (Science, 1997, 278:1041-1042).*
Byers, T. (CA Cancer Journal, vol. 49, No. 6, Nov./Dec. 1999).*
Krontiris and Capizzi (Internal Medicine, 4th Edition, Editor-in-chief Jay Stein, Elsevier Science, 1994 Chapters 71-72, pp. 699-729).*
Carter, S. K. et al. (Chemotherapy of Cancer; Second edition; John Wiley & Sons: New York, 1981; appendix C).*
Kaiser (Science, 2006, 313: 1370).*
Bird, C. "GenBank DDBJ databases", XP-002363633 Nucleotide Sequence retrieved from Uniprot Database accession No. Q5JWQ2 May 10, 2005 , 1.
Du, H. L. et al., "Improving the comparative map of SSC15q21-q26 containing QTL for reproduction in EMBL GenBank DDBJ databases", XP-002363734 retrieved from Uniprot Database assession No. Q5RLQ5_Pig Feb. 1, 2005 , 1.
Lowbridge, John et al., "Studies on the Extended Active Site of Papain", *The Journal of Biological Chemistry*, vol. 249, No. 21, Nov. 10, 1974 , 6754-6761.
Russ, William P. et al., "The GxxxG Motif: A Framework for Transmembrane Helix-Helix Association", *Journal of Molecular Biology*, vol. 296, No. 3 Feb. 25, 2000 , 911-919.
Schneider, Dirk et al., "Involvement of Transmembrane Domain Interactions in Signal Transduction of ab Integrins", *The Journal of Biological Chemistry*, vol. 279, No. 11, Mar. 12, 2004 , 9840-9846.
Williams, Gareth et al., "A complementary peptide approach applied to the design of novel semaphorin/neuropilin antagonists", *Journal of Neurochemistry*, 92 2005 , 1180-1190.

* cited by examiner

*Primary Examiner* — Mark Halvorson
*Assistant Examiner* — Yan Xiao
(74) *Attorney, Agent, or Firm* — Kilpatrick Townsend & Stockton LLP

(57) ABSTRACT

The present invention concern a peptidic antagonist of class III semaphorins/neuropilins complexes comprising an amino acid sequence, which is derived from the transmembrane domain of a protein selected in the group consisting of neuropilin-1, neuropilin-2, plexin-A1, plexin-A2, plexin-A3, plexin-A4, Nr-CAM, L1-CAM, integrin Beta 1 and integrin beta 2, and including at least a GxxxG motif, eventually fused to an heterologous sequence; a nucleic acid encoding for said peptidic antagonist, a pharmaceutical composition comprising such a peptidic antagonist or a nucleic acid encoding thereof and uses thereof.

4 Claims, 13 Drawing Sheets

Transmembrane domains (*Mus musculus*)

Neuropiline 1 P97333 857-879 (SEQ ID NO. 1) ILITIIAMSAL<u>GVLLGAVCG</u>VVL

Neuropiline 2 O35375 865-889 (SEQ ID NO. 2) ILITIIAMSSL<u>GVLLGATCAG</u>LLLY

Plexin A1 P70206 1238-1264 (SEQ ID NO. 3) LLTLPAIV<u>GIGGGGG</u>LLLLVIVAVLIA

Plexin A2 P70207 1223-1250 (SEQ ID NO. 6) LLTLPAII<u>SIAAGG</u>SLLLIIVIIVLIAY

Plexin A3 P70208 1216-1243 (SEQ ID NO. 5) LTLPAMV<u>GLAAGGG</u>LLLLAITVVLVAY

Plexin A4 Q80UG2 1230-1255 (SEQ ID NO. 6) LSLPAIV<u>SIAVAGG</u>LLIIFIVAVLIA

Nr-CAM Q810U4 1120-1142 (SEQ ID NO. 7) <u>GWFIGLMCAVALLILILLIVCFI</u>

L1-CAM P11627 1123-1146 (SEQ ID NO. 8) <u>GWFIAFVSAIILLLLILLILCFI</u>

Integrin beta-1   P09055 729-751      IIPIV<u>AGVVAGIV</u>LIGLALLLIW (SEQ ID NO. 9)

Integrin beta-2   P11835 703-725      VAAIVGGT VV<u>GVVLIG</u>VL LLVIW
(SEQ ID NO. 10)

Figure 1

Transmembrane domains (*Homo sapiens*)

| | | | |
|---|---|---|---|
| Neuropiline 1 | O14786 857-879 | ILITIIAMSAL<u>GVLLGAVCG</u>VVL | (SEQ ID NO. 1) |
| Neuropiline 2 | O60462 865-889 | ILITIIAMSSL<u>GVLLGATCAG</u>LLLY | (SEQ ID NO. 2) |
| Plexin A1 | Q9UIW2 1218-1244 | LLTLPAIV<u>GIGGGGG</u>LLLLVIVAVLIA | (SEQ ID NO. 3) |
| Plexin A2 | Q5JRL6 1232-1260 | LLTLPAIV<u>SIAAG</u>GSLLLIIVIIVLIAY | (SEQ ID NO. 11) |
| Plexin A3 | P51805 1216-1241 | LTLPAMM<u>GLAAG</u>GGLLLLAITAVLVA | (SEQ ID NO. 12) |
| Plexin A4 | Q9HCM2 688-713 | LSLPAIVSI<u>AVAGG</u>LLIIFIVAVLIA | (SEQ ID NO. 6) |
| Nr-CAM | Q92823 1168-1190 | <u>GWFIG</u>LMCAVALLILILLIVCFI | (SEQ ID NO. 7) |
| L1-CAM | P32004 1121-1143 | <u>GWFIG</u>FVSAIILLLLVLLIL | (SEQ ID NO. 13) |
| Integrin beta-1 | P05556 729-751 | IIPIVA<u>GVVAG</u>IVLIGLALLLIW | (SEQ ID NO. 9) |
| Integrin beta-2 | P05107 701-723 | IAAIVG<u>GTVAG</u>IVLIGILLLVIW | (SEQ ID NO. 16) |

Figure 2

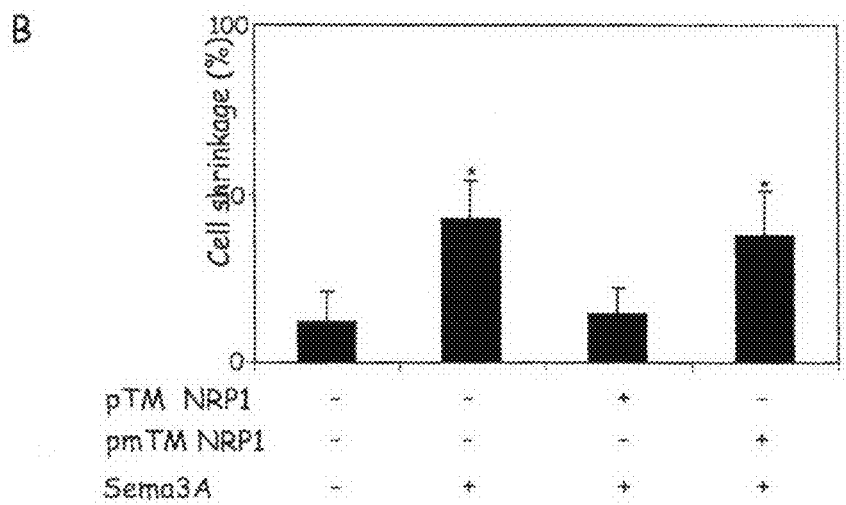
Figure 5

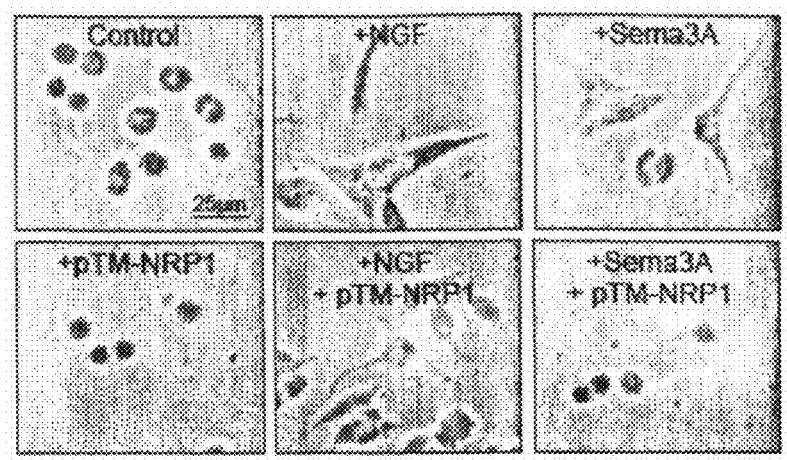
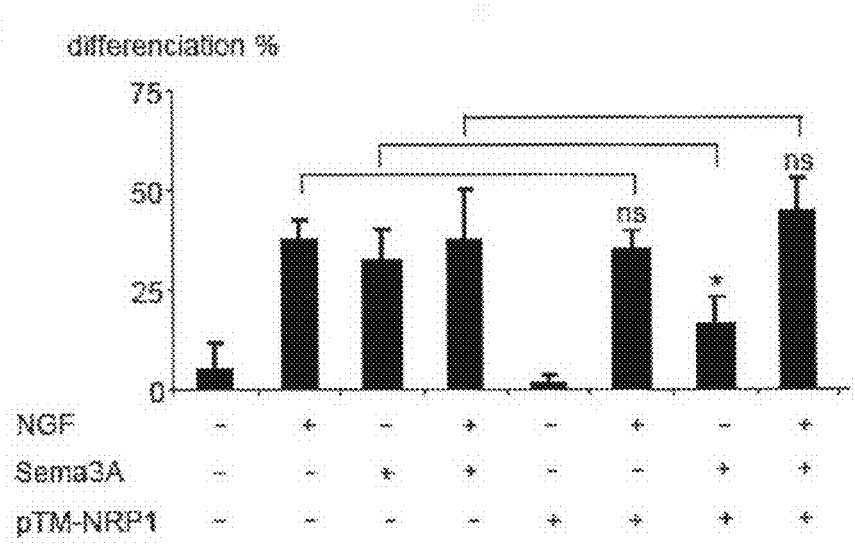
Figure 8

PEPTIDIC ANTAGONISTS OF CLASS III SEMAPHORINS/NEUROPILINS COMPLEXES

RELATED APPLICATIONS

This application is a national stage filing under 35 U.S.C. §120 or 35 U.S.C. §365(c) of International Application No. PCT/IB2006/002334, filed 28 Jun. 2006, which claims priority to European Application No. 05291392.8 filed on 28 Jun. 2005, the contents of which are incorporated by reference herein.

The present invention relates to peptidic antagonists of class III semaphorins/neuropilins complexes, and uses thereof.

BACKGROUND OF THE INVENTION

Next to its structural and trophic roles, the extra cellular matrix (ECM) defines an ideal environment for cell to cell communication and determines all the cellular behaviors, including proliferation, migration, differentiation or apoptosis. The molecular mechanisms controlling these processes are getting better understood. In the nervous system, 3 major families of diffusible or transmembrane signals (netrins, semaphorins and ephrins ensure these functions during embryonic development. (TESSIER-LAVIGNE and GOODMAN, *Science*, vol. 274, p: 1123-33, 1996). Among them, the semaphorins define a family of more than 25 members subdivided into 8 classes according to their structural specificities (KOLODKIN et al., *Cell*, vol. 75, p: 1389-99, 1993) and which can be classified as either secreted or transmembrane semaphorins. The secreted ones are class II (invertebrates), III (vertebrates), and V (viral), whereas the other classes (I, IV and VI-VIII) are transmembrane.

Over the past five years, several studies were designed to elucidate the transduction pathways allowing the signaling of the diverse functions of semaphorins ranging from axon guidance, cell migration, cell differentiation to apoptosis in both physiological and pathological conditions. The current view considers that this functional diversity is due to the formation of a receptor complex, highly dynamic, modulating signal integration by selective recruitment and activation of multiple intracellular pathways leading to actin cytoskeleton remodeling (CASTELLANI and ROUGON, *Curr. Opin. Neurobiol.*, vol. 12, p: 532-41, 2002). All of them have a common domain called the "sema" domain of nearly 500 amino acids with 12-16 cysteine residues, which confers the binding specificity of each semaphorin (RAPER, *Curr. Opin. Neurobiol.*, vol. 10, p: 88-94, 2000). Among these different semaphorins, class III semaphorins induce the collapse of neuronal growth cones, which is why they were initially named collapsins (LUO et al., *Cell*, vol. 75, p: 217-227, 1993). Sema 3A, the molecule that gives the rest of the family its name, is the most extensively studied, and in all cases it has been described as a repellent factor for axons, from sensory neurons and spinal motoneurons to pyramidal neurons of the cortex (MUELLER, *Annu. Rev. Neurosci.*, vol. 22, p: 351-388, 1999). Strikingly, this semaphorin can exert two different effects in the same cell. This has been demonstrated in cortical neurons in which Sema3A acts as a repellent factor for axons and is a chemoattractant for the dendrites (POLLEUX et al., *Nature*, vol. 404, p: 567-73, 2000; BAGNARD et al., *Development*, vol. 125(24), p: 5043-53, 1998). In order to explain this phenomenon, it is necessary to consider the existence of a mechanism ensuring a differential transduction in the two cellular poles. More than a principle of differential transduction, it is necessary to understand the mechanisms controlling the molecular hierarchy and to elucidate the formation of supra-molecular structures ensuring the diversity of the cellular behaviors in response to environmental changes.

Hence, recent works demonstrated the role of the two known members of the neuropilin family, neuropilin-1 (NRP1) and neuropilin-2 (NRP2), as the ligand binding sub units of the receptor complex involved in the transduction cascade of class III semaphorins (for review see Bagnard D. (Editor) Neuropilin: from nervous system to vascular and tumor biology. Landes Bioscience-Kluwer Academic/Plenum Publishers Hardbound, ISBN 0-306-47416-6, *Advance in Experimental Medicine and Biology* Vol. 515, p: 140, 2002). NRP1 and NRP2 are single spanning transmembrane proteins with an (i) extracellular part, which is important for dimerization (RENZI et al., *J. Neurosci.*, vol. 19, p: 7870-7880, 1999), a transmembrane segment, and a short cytoplasmic domain of about 40 amino acids.

Interestingly, NRP1 and NRP2 possess a short intracellular domain without transduction capacity. A molecular explanation for this observation was given when it was found that neuropilins form complexes with receptors belonging to the plexin family, and that the plexin is the transducing element in neuropilin/plexin complex (RHOM et al., *Mech. Dev.*, vol. 93, p: 95-104, 2000; TAMAGONE et al., *Cell*, vol. 99, p: 71-80, 1999). Finally, signal transduction by class III semaphorins depends upon complex formation between neuropilins with the plexins.

Nevertheless, complexes with plexins are not the only types of complexes formed by neuropilins.

It was found that neuropilins can also form stable complexes with the adhesion molecules L1-CAM and Nr-CAM (CASTELLANI et al., *Neuron*, vol. 27, p: 237-249, 2000) and mutations in the extracellular domain of L1 or the complete absence of L1 in gene-targeted mice result in the disruption of Sema 3A signaling leading to guidance errors.

Tyrosine kinase receptors may, therefore, also play a role in neuropilin-associated signaling. Thus, it has been observed that the migration of DEV neuroectodermal progenitor cells is repulsed by Sema 3A, and the presence of both NRP1 and VEGFR-1 is required for the repulsion (Bagnard et al., *J Neurosci.*, vol. 21, p: 3332-41, 2001). This interaction explain the inhibition of sprout formation by VEGF in an in vitro model of angiogenesis with Sema 3A (MIAO et al., *J. Cell. Biol.*, vol. 146, p: 233-242, 1999). It has also been found that neuropilins form complexes with VEGFR-2 (SORER et al., *Cell*, vol. 92, p: 735-45, 1998) and MET (WINBERG et al., *Neuron*, vol. 32, p: 53-62, 2001).

Recently, it has also been shown that neuropilins form complexes with integrins, and said complexes are able to promote axon outgrowth (PASTERRAMP et al., *Nature*, vol. 424, p: 398-405, 2003).

Consequently, the above studies contribute to identify class III semaphorins/neuropilins complexes as a potential target for neurodegenerative conditions and cancer as recently evidence (for a review see GUTTMANN-RAVIV et al., *Cancer Letter*, 2006; CHEDOTAL et al., *Cell Death and Differentiation*, 2005). In this context, agents that interfere with the complex formation would clearly have therapeutic potential and/or be useful biological tools.

In this way, GARETH et al. (*Journal of Neurochemistry*, vol. 92, p: 1180-1190, 2005) have used an algorithm in order to design a peptide antagonist of Sema 3A/NRP1 complex. The authors have identified antagonist peptides in the Sema 3A Ig domain, which is implicated in Sema 3A/NRP1 dimerization, and a NRP1 MAM domain, which mediates the lateral dimerization of the receptor but not the ligand binding.

The identified antagonist peptides are able to effectively inhibit the growth cone collapse response stimulated by Sema 3A. Nevertheless, these antagonists, which are not located in the transmembrane domain, have an IC50 of more than 1 µM, said concentration being too important to enable the use of such an antagonist in therapy.

So, there is a recognized and permanent need in the art for new antagonists of class III semaphorins/neuropilins complexes, which can be used in therapies.

DESCRIPTION OF THE INVENTION

The purpose of the present invention is to fulfil this need by providing new antagonists having a greater activity.

Unexpectedly, the inventors have demonstrated that a peptide corresponding to the transmembrane domain of NRP1 can inhibit the cortical axons collapses induced by Sema 3A with an IC50 of less than $10^{-11}$ M. This peptide includes two consecutive GxxxG dimerization motifs (where x represents any amino acid), said GxxxG motif was firstly identified in Glycophorin A (SENES et al., *J. Mol. Biol.*, vol. 296, p: 921-36, 2000). Such a motif has also been shown as operative in the dimerization of TM segments of erbB receptors (MENDROLA et al., *J. Biol. Chem.*, vol. 277, p: 4704-12, 2002). In general any motif composed of small amino acid-XXX-small amino acid (where the definition of a small amino acid is well known from one of skill in the art) possesses equivalent properties.

The NRP1 double GxxxG motif is highly conserved and presents a strong homology to the one of NRP2 (FIG. 1). Finally, such motifs are found in the transmembrane domains of multiple partners of neuropilins including members of the Plexin family, Nr- and L1-CAM, and integrins. Altogether, the results obtained by the inventors suggest that the transmembrane domains of these proteins have a key role in the formation and modulation of the complexes ensuring semaphorin signaling.

Consequently, in one aspect the present invention relates to a peptidic antagonist of class III semaphorins/neuropilins complexes comprising an amino acid sequence, which is derived from the transmembrane domain of a protein selected in the group consisting of neuropilin-1, neuropilin-2, plexin-A1, plexin-A2, plexin-A3, plexin-A4, Nr-CAM, L1-CAM, integrin beta 1 and integrin beta 2, and including at least one GxxxG motif, optionally fused to an heterologous sequence.

As used herein an "heterologous sequence" relates to any amino acid sequence which is not derived from neuropilin-1, neuropilin-2, plexin-A1, plexin-A2, plexin-A3, plexin-A4, Nr-CAM, L1-CAM, integrin beta 1 or integrin beta 2. This heterologous sequence can for example allows a specific cellular location or a better purification yield (e.g. His tag) of the peptidic antagonist of the invention.

As used herein the term "peptidic antagonist of class III semaphorins/neuropilins complexes" relates to a synthetic or recombinant polypeptide, which interferes with said complexes formation and finally the signal transduction of such complexes. Consequently, the peptidic antagonists of the invention does not include the complete neuropilin-1, neuropilin-2, plexin-A1, plexin-A2, plexin-A3, plexin-A4, Nr-CAM, L1-CAM, integrin beta 1, and integrin beta 2 proteins.

As used herein "a transmembrane domain" corresponds to peptidic domain traversing the cell's membrane. Said domain is hydrophobic and has an α-helical structure. One of skill in the art can simply identify such domains in said proteins according to its general knowledge. As an example, the hydrophobicity of a proteic domain can be determined by the Kyte & Doolittle method, and the potentiality of a proteic domain to form an α-helical structure can be determined by the Chou & Fasman method. Such methods are notably available at the following address www.expasy.org/tools/protscale.html.

The amino acid sequence of the transmembrane domain of neuropilin-1, neuropilin-2, plexin-A1, plexin-A2, plexin-A3, plexin-A4, Nr-CAM, L1-CAM, integrin beta 1 and integrin beta 2 are well conserved and can be simply identified from the complete amino acid sequence of the protein, which are well known from one of skill in the art. As an example, one can cite the neuropilin-1 amino acid sequence from *Mus musculus* (P97333), *Homo sapiens* (O14786), *Rattus norvegicus* (Q9QWJ9), Zebrafish (Q8QFX6) and *Gallus gallus* (P79795), the neuropilin-2 amino acid sequence from *Homo sapiens* (O60462), *Mus musculus* (O35375), *Rattus norvegicus* (NP_110496) and *Gallus gallus* (NP_989615), the plexin A-1 amino acid sequence from *Homo sapiens* (NP_115618, Q9UIW2) and *Mus musculus* (NP_032907, P70206), the plexin A-2 amino acid sequence from *Homo sapiens* (CAI40198, Q5JRL6) and *Mus musculus* (NP_032908, P70207), the plexin A3 amino acid sequence from *Homo sapiens* (NP_032907, P51805), *Xenopus tropicalis* (CAI40198) and *Mus musculus* (NP_032909, P70208), the plexin A4 amino acid sequence from *Mus musculus* (NP_786926, Q80UG2), *Homo sapiens* (Q9HCM2) and *Danio rerio* (NP_001004495), the Nr-CAM amino acid sequence from *Mus musculus* (Q810U4), *Rattus norvegicus* (P97686), *Homo sapiens* (Q92823) and *Gallus gallus* (P35331), the L1-CAM amino acid sequence from *Homo sapiens* (P32004), *Takifugu rubripes* (Q98902), *Mus musculus* (P11627) and *Rattus norvegicus* (Q05695), the integrin beta 1 amino acid sequence from *Mus musculus* (P09055), *Homo sapiens* (P05556), *Felis catus* (P53713), *Rattus norvegicus* (P49134), *Xenopus laevis* (P12606) and *Gallus gallus* (P07228), and the integrin beta 2 amino acid sequence from *Mus musculus* (P11835), *Homo sapiens* (P05107), *Sus scrofa* (P53714), *Bos taurus* (P32592) and *Sigmodon hispidus* (AAL38579).

The FIG. 1 shows the transmembrane domains of mouse neuropilin-1 (SEQ ID NO. 1: ILITIIAMSALGVLLGAVCGVVL), neuropilin-2 (SEQ ID NO. 2: ILITIIAMSSLGVLLGATCAGLLLY), plexin A1 (SEQ ID NO. 3: LLTLPAIVGIGGGGGLLLLVIVAVLIA), plexin A2 (SEQ ID NO. 4: LLTLPAIISIAAGGSLLLIIVIIVLIAY), plexin A3 (SEQ ID NO. 5: LTLPAMVGLAAGGGLLLLAITVVLVAY), plexin A4 (SEQ ID NO. 6: LSLPAIVSIAVAGGLLIIFIVAVLIA), Nr-CAM (SEQ ID NO. 7: GWFIGLMCAVALLILLLIVCF), L1-CAM (SEQ ID NO. 8: GWFIAFVSAIILLLLILLILCFI), integrin beta 1 (SEQ ID NO. 9: IIPIVAGVVAGIVLIGLALLLIW) and integrin beta 2 (SEQ ID NO. 10: VAAIVGGTVVGVVLIGVLLLVIW). The term "GxxxG motif" relates to the motif as identified in SENES et al. (above mentioned, 2000), which is shown in FIG. 1 (underlined). Potential "GxxxG" motif are also shown (dotted line).

The conservation of these transmembrane domains clearly stands out from the FIG. 2, which shows the same transmembrane domains for human neuropilin-1 (SEQ ID NO. 1: ILITIIAMSALGVLLGAVCGVVL), neuropilin-2 (SEQ ID NO. 2: ILITIIAMSSLGVLLGATCAGLLLY), plexin A1 (SEQ ID NO. 3: LLTLPAIVGIGGGGGLLLLVIVAVLIA), plexin A2 (SEQ ID NO. 11: LLTLPAIVSIAAGGSLLLIIVIIVLIAY), plexin A3 (SEQ ID NO. 12: LTLPAMMGLAAGGGLLLLAITAVLVA), plexin A4 (SEQ ID NO. 6: LSLPAIVSIAVAGGLLIIFIVAVLIA), Nr-CAM (SEQ ID NO. 7: GWFIGLMCAVALLILILLLIVCFI), L1-CAM (SEQ ID NO. 13: GWFIGFVSAIILLLLVLLIL), integrin beta 1

(SEQ ID NO. 9: IIPIVAGVVAGIVLIGLALLLIW) and integrin beta 2 (SEQ ID NO. 14: IAAIVGGTVAGIVLIGILLLVIW).

As another example of this conservation, one can cite the neuropilin-1 transmembrane domain from *Gallus gallus* (SEQ ID NO. 14: ILITIIAMSALGVLLGAICGVVL), and from Zebrafish (SEQ ID NO. 15: ILITIIAMSALGVFLGAICGVVL), and the neuropilin-2 transmembrane domain from *Gallus gallus* (SEQ ID NO. 16: ILITIIAMSSLGVLLGATCAGLLLY), which share an identity of more than 90% with the human neuropilin-1 and neuropilin-2 transmembrane domain respectively.

According to a preferred embodiment, the invention relates to a peptidic antagonist of class III semaphorins/neuropilins complexes comprising an amino acid sequence, which is derived from the transmembrane domain of a protein selected in the group consisting of human neuropilin-1 (SEQ ID NO. 1: ILITIIAMSALGVLLGAVCGVVL), neuropilin-2 (SEQ ID NO. 2: ILITIIAMSSLGVLLGATCAGLLLY), plexin A1 (SEQ ID NO. 3: LLTLPAIVGIGGGGGLLLLVIVAVLIA), plexin A2 (SEQ ID NO. 11: LLTLPAIVSIAAGGSLLLIIVIIVLIAY), plexin A3 (SEQ ID NO. 12: LTLPAMMGLAAGGGLLLLAITAVLVA), plexin A4 (SEQ ID NO. 6: LSLPAIVSIAVAGGLLIIFIVAVLIA), Nr-CAM (SEQ ID NO. 7: GWFIGLMCAVALLILILLIVCFI), L1-CAM (SEQ ID NO. 13: GWFIGFVSAIILLLLVLLIL), integrin beta 1 (SEQ ID NO. 9: IIPIVAGVVAGIVLIGLALLLIW) and integrin beta 2 (SEQ ID NO. 14: IAAIVGGTVAGIVLIGILLLVIW), and including at least one GxxxG motif, optionally fused to an heterologous sequence.

According to another preferred embodiment, said peptidic antagonist of class III semaphorins/neuropilins complexes comprises an amino acid sequence, which is derived from the human neuropilin-1 (SEQ ID NO. 1, ILITIIAMSALGVLLGAVCGVVL) or neuropilin-2 (SEQ ID NO. 2, ILITIIAMSSLGVLLGATCAGLLLY) transmembrane domain, optionally fused to an heterologous sequence.

According to still another preferred embodiment, said peptidic antagonist of class III semaphorins/neuropilins complexes comprises an amino acid, sequence, which is derived from the transmembrane domain of a protein including at least two GxxxG motifs, preferably at least two consecutive GxxxG motifs, and selected in the group consisting of human neuropilin-1 (SEQ ID NO. 1, ILITIIAMSALGVLLGAVCGVVL), integrin beta 1 (SEQ ID NO. 9: IIPIVAGVVAGIVLIGLALLLIW) and integrin beta 2 (SEQ ID NO. 14: IAAIVGGTVAGIVLIGILLLVIW) transmembrane domain, optionally fused to an heterologous sequence.

Preferably, the peptidic antagonist of the invention comprises an amino acid sequence derived from the human neuropilin-1 transmembrane domain (SEQ ID NO. 1, ILITIIAMSALGVLLGAVCGVVL).

Advantageously, said amino acid sequence which is derived from a transmembrane domain of one of the proteins above described is more than 10 amino acids length, preferably more than 14 amino acids length, as an example more than 18 amino acids length, and more preferably more than 22 amino acids.

Advantageously, said amino acid sequence which is derived from one of the proteins selected in the group consisting of neuropilin-1, neuropilin-2, plexin-A1, plexin-A2, plexin-A3, plexin-A4, Nr-CAM, L1-CAM, integrin beta 1 and integrin beta 2 is less than 150 amino acids in length, preferably less than 100 amino acids in length, more preferably less than 50 amino acids in length.

According to a preferred embodiment, the peptidic antagonists derived from neuropilin-1 and neuropilin-2 do not include their extracellular domains associated with class III semaphorins dimerization. These domains are well known from one of skill in the art and are described in NEUFELD et al. (*TCM*, vol. 12(1), p: 13-19, 2002) and in BAGNARD (2002, above mentioned). For example, these domains include the a (CUB domain, also called a1 and a2 domains ensuring semaphorin binding), b (homologue domain to coagulation factor V/VIII; subdivided into b1 and b2 domains, b1 being involved in the binding of VEGF isoforms), c (MAM domain, involved in the dimerization of NRP1) domains of NRP1 and NRP2.

Advantageously, said peptidic antagonist consists of an amino acid sequence selected in the group consisting of plexin A1 (SEQ ID NO. 3: LLTLPAIVGIGGGGGLLLLVIVAVLIA), plexin A2 (SEQ ID NO. 11: LLTLPAIVSIAAGGSLLLIIVIIVLIAY), plexin A3 (SEQ ID NO. 12: LTLPAMMGLAAGGGLLLLAITAVLVA), plexin A4 (SEQ ID NO. 6: LSLPAIVSIAVAGGLLIIFIVAVLIA), Nr-CAM (SEQ ID NO. 7: GWFIGLMCAVALLILILLIVCFI), L1-CAM (SEQ ID NO. 13: GWFIGFVSAIILLLLVLLIL), integrin beta 1 (SEQ ID NO. 9: IIPIVAGVVAGIVLIGLALLLIW) and integrin beta 2 (SEQ ID NO. 14: IAAIVGGTVAGIVLIGILLLVIW) transmembrane domains, or derivatives thereof, optionally fused to an heterologous sequence.

According to a second preferred embodiment, the peptidic antagonists derived from plexin-A1, plexin-A2, plexin-A3, plexin-A4, integrin beta1, integrin beta2, Nr-CAM and L1-CAM do not include their intracellular domains associated with signal transducing pathways. These domains are well known from one of skill in the art and are described in BAGNARD (above mentioned, 2002) and include for example but not exclusively the Sex-Plexin domain, the PH1A and PH2A domains or the PRB (Plexin Rac binding domain) domain.

Advantageously, said peptidic antagonist consists of an amino acid sequence selected in the group consisting of neuropilin-1 (SEQ ID NO. 1: ILITIIAMSALGVLLGAVCGVVL) and neuropilin-2 (SEQ ID NO. 2: ILITIIAMSSLGVLLGATCAGLLLY) transmembrane domains, or derivatives thereof, optionally fused to an heterologous sequence. Preferably, said peptidic antagonist consists of neuropilin-1 (SEQ ID NO. 1: ILITIIAMSALGVLLGAVCGVVL) transmembrane domain, or derivatives thereof, optionally fused to an heterologous sequence.

An amino acid sequence "derived from" or a "derivative of" the transmembrane domain of human neuropilin-1 (SEQ ID NO. 1: ILITIIAMSALGVLLGAVCGVVL), neuropilin-2 (SEQ ID NO. 2: ILITIIAMSSLGVLLGATCAGLLLY), plexin A1 (SEQ ID NO. 3: LLTLPAIVGIGGGGGLLLLVIVAVLIA), plexin A2 (SEQ ID NO. 11: LLTLPAIVSIAAGGSLLLIIVIIVLIAY), plexin A3 (SEQ ID NO. 12: LTLPAMMGLAAGGGLLLLAITAVLVA), plexin A4 (SEQ ID NO. 6: LSLPAIVSIAVAGGLLIIFIVAVLIA), Nr-CAM (SEQ ID NO. 7: GWFIGLMCAVALLILILLIVCFI), L1-CAM (SEQ ID NO. 13: GWFIGFVSAIILLLLVLLIL), integrin beta1 (SEQ ID NO. 9: IIPIVAGVVAGIVLIGLALLLIW) or integrin beta2 (SEQ ID NO. 14: IAAIVGGTVAGIVLIGILLLVIW) transmembrane domain relates to amino acid sequence having an identity of more than 60% with said transmembrane domains or fragments thereof, for example of more than 70% or of more than 80%, preferably of more than 85%, most preferably of more than 90% and advantageously of more than 95%.

As used herein, "a fragment of a transmembrane domain" relates to a polypeptide which is more than 10 amino acids length, preferably more than 14 amino acids length, as an example more than 18 amino acids length, and more preferably more than 22 amino acids.

The identity differences between the above described transmembrane domains and the amino acid sequence of the peptidic antagonist of the invention result from amino acids substitution in the transmembrane domain amino acid sequences of the peptidic antagonist.

Preferably, the substituted amino acid(s) in these transmembrane domains is (are) neutral and/or hydrophobic amino acids, and most preferably hydrophobic amino acids. Such neutral and hydrophobic amino acids are well known from one of skill in the art.

According to a specific embodiment, said transmembrane domain amino acid sequences have an identity of 100% with said transmembrane domains or fragments thereof.

In a second aspect the present invention relates to a nucleic acid encoding for a peptidic antagonist as described above.

Said nucleic acid corresponds to RNA or DNA, preferably to DNA.

According to a preferred embodiment, the nucleic acid encoding the peptidic antagonist is operatively linked to a gene expression sequence, which directs the expression of nucleic acid within a prokarotic or an eukaryotic cell, preferably an eukaryotic cell. The "gene expression sequence" is any regulatory nucleotide sequence, such as a promoter sequence or promoter-enhancer combination, which facilitates the efficient transcription and translation of the peptidic antagonist nucleic acid to which it is operatively linked and any signal sequence ensuring appropriate targeting of the peptidic antagonist to the plasma membrane. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPTR), adenosine deaminase, pyruvate kinase, beta.-actin promoter, muscle creatine kinase promoter, human elongation factor promoter and other constitutive promoters. Exemplary viral promoters which function constitutively in eukaryotic cells include, for example, promoters from the simian virus (e.g., SV40), papilloma virus, adenovirus, human immunodeficiency virus (HIV), cytomegalovirus (CMV), Rous sarcoma virus (RSV), hepatitis B virus (HBV), the long terminal repeats (LTR) of Moloney leukemia virus and other retroviruses, and the thymidine kinase promoter of herpes simplex virus. Others constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Others inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined antigen nucleic acid. The gene expression sequences optionally include enhancer sequences or upstream activator sequences as desired.

As used herein, the peptidic antagonist nucleic acid sequence and the gene expression sequence are said to be "operably linked" when they are covalently linked in such a way as to place the expression or transcription and/or translation of the peptidic antagonist coding sequence under the influence or control of the gene expression sequence. Two DNA sequences are said to be operably linked if induction of a promoter in the 5' gene expression sequence results in the transcription of the peptidic antagonist sequence and if the nature of the linkage between the two DNA sequences does not (1) result in the introduction of a frame-shift mutation, (2) interfere with the ability of the promoter region to direct the transcription of the peptidic antagonist sequence, or (3) interfere with the ability of the corresponding RNA transcript to be translated into a protein. Thus, a gene expression sequence would be operably linked to a peptidic antagonist nucleic acid sequence if the gene expression sequence were capable of effecting transcription of that antigen nucleic acid sequence such that the resulting transcript is translated into the desired protein or polypeptide.

The peptidic antagonist nucleic acid may be delivered in vivo alone or in association with a vector. In its broadest sense, a "vector" is any vehicle capable of facilitating the transfer of the peptidic antagonist nucleic acid to the cells and preferably cells expressing neuropilins. Preferably, the vector transports the nucleic acid to cells with reduced degradation relative to the extent of degradation that would result in the absence of the vector. The vector optionally includes the above-described gene expression sequence to enhance expression of the peptidic antagonist nucleic acid in neuropilins' expressing cells. In general, the vectors useful in the invention include, but are not limited to, plasmids, phagemids, viruses, other vehicles derived from viral or bacterial sources that have been manipulated by the insertion or incorporation of the peptidic antagonist nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in KRIEGLER (A Laboratory Manual, W.H. Freeman C.O., New York, 1990) and in MURRY ("Methods in Molecular Biology," vol. 7, Humana Press, Inc., Cliffton, N.J., 1991):

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g., SANBROOK et al., "Molecular Cloning: A Laboratory Manual," Second Edition, Cold Spring Harbor Laboratory Press, 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

The nucleic acid vector can include selectable markers that are active both in bacteria and in mammalian cells.

According to a first specific embodiment, the nucleic acid vector of the present invention corresponds to "naked DNA" like plasmids, cosmids or phagemids. Such naked DNA can be associated with non-lipid cationic polymers (WU and WU, *J. Biol. Chem.*, vol. 263, p: 14621-4, 1988) or liposomes (BRIGHMAN et al., *Am. J. Med. Sci.*, vol. 298, p: 278-81, 1989) to form complexes enhancing cellular uptake.

According to a second specific embodiment, the nucleic acid vector is a viral vector adapted for in vivo gene therapy protocols. Examples of appropriate viral vectors includes retroviral vectors as described in EP 0871459, EP 0386882 and EP 1222300 and adenovirus vectors as described in US 2004/265273 and U.S. Pat. No. 6,638,502. In this case, the internalization of virus occurs through the specific interaction of the viral envelope with a cell surface receptor, followed by receptor-mediated endocytosis of the virus/receptor complex.

In a third aspect the present invention relates to a composition comprising a peptidic antagonist as described above, a nucleic acid encoding thereof, or a nucleic acid vector comprising said nucleic acid, eventually associated with a pharmaceutically acceptable vehicle.

As an example of pharmaceutically acceptable vehicle, the composition may comprise emulsions, microemulsions, oil-in-water emulsions, anhydrous lipids and oil-in-water emulsions, other types of emulsions. The composition may also comprise one or more additives (e.g., diluents, excipients, stabilizers, preservatives). See, generally, Ullmann's Encyclopedia of Industrial Chemistry, $6^{th}$ Ed. (various editors, 1989-1998, Marcel Dekker); and Pharmaceutical Dosage Forms and Drug Delivery Systems (ANSEL et al., 1994, WILLIAMS & WILKINS).

Advantageously, said composition comprise a concentration of said peptidic antagonist of more than $10^{-12}$ M, preferably more than $10^{-11}$ M and most preferably more than $10^{-10}$ M.

Peptidic antagonists, nucleic acids or nucleic acid vectors may be solubilized in a buffer or water or incorporated in emulsions and microemulsions. Suitable buffers include, but are not limited to, phosphate buffered saline $Ca^{++}/Mg^{++}$ free (PBS), phosphate buffered saline (PBS), normal saline (150 mM NaCl in water), Tris buffer and surfactants.

There are numerous causes of peptide instability or degradation, including hydrolysis and denaturation. Hydrophobic interaction may cause clumping of molecules together (i.e. aggregation). This result may entail diminution of the induction of a Treg response. Stabilizers may be added to lessen or prevent such problems.

Stabilizers include cyclodextrine and derivatives thereof (see U.S. Pat. No. 5,730,969). Suitable preservatives such as sucrose, mannitol, sorbitol, trehalose, dextran and glycerin can also be added to stabilize the final formulation. A stabilizer selected from ionic and non-ionic surfactants, D-glucose, D-galactose, D-xylose, D-galacturonic acid, trehalose, dextrans, hydroxyethyl starches, and mixtures thereof may be added to the formulation. Addition of alkali metal salt or magnesium chloride may stabilize a peptide. The peptide may also be stabilized by contacting it with a saccharide selected from the group consisting of dextran, chondroitin sulphuric acid, starch, glycogen, dextrin, and alginic acid salt. Other sugars that can be added include monosaccharides, disaccharides, sugar alcohols, and mixtures thereof (E.g., glucose, mannose, galactose, fructose, sucrose, maltose, lactose, mannitol, xylitol). Polyols may stabilize a peptide, and are water-miscible or water-soluble. Suitable polyols may be polyhydroxy alcohols, monosaccharides and disaccharides including mannitol, glycrol, ethylene glycol, propylene glycol, trimethyl glycol, vinyl pyrrolidone, glucose, fructose, arabinose, mannose, maltose, sucrose, and polymers thereof. Various excipients may also stabilize peptides, including serum albumin, amino acids, heparin, fatty acids and phospholipids, surfactants, metals, polyols, reducing agents, metal chelating agents, polyvinyl pyrrolidone, hydrolysed gelatin, and ammonium sulfate.

In a fourth aspect the present invention relates to a method of prophylactic or therapeutic treatment of a subject suffering from a disease associated with class III semaphorins/neuropilins complexes signal transduction pathways comprising the step of administrating a composition as described above to said subject.

As used herein, the term "subject" denotes a Mammal, such as a rodent, a feline, a canine and a primate. The subject is an animal such as cow, pig, horse, cat, dog and most preferably a human.

A disease associated with class III semaphorins/neuropilins complexes signal transduction pathways can be simply determined by one of skill in the art. As an example of such diseases, one can cite neurodegenerative diseases (like Alzheimer disease, Parkinson disease, central nervous system lesions, demyelination associated pathologies), cancers (like lung, breast and mesothelial cancers, carcinoma or glioma), and all diseases associated to abnormal angiogenesis.

Advantageously, said administration of said composition corresponds to a concentration of said peptidic antagonist of more than $10^{-12}$ M, preferably more than $10^{-11}$ M and most preferably more than $10^{-10}$ M.

In a fifth aspect the present invention relates to the use of a peptidic antagonist as described above, a nucleic acid encoding thereof, or a nucleic acid vector comprising said nucleic acid for the manufacture of a medicament for the prevention or treatment of a subject suffering of a disease associated with class III semaphorins/neuropilins complexes signal transduction pathways.

A disease associated with class III semaphorins/neuropilins complexes signal transduction pathways can be simply determined by one of skill in the art. As an example of such diseases, one can cite neurodegenerative diseases (like Alzheimer disease, Parkinson disease, central nervous system lesions, demyelination associated pathologies), cancers (like lung, breast and mesothelial cancers, carcinoma or glioma), and all diseases associated to abnormal angiogenesis.

In a preferred embodiment, the present invention relates to the use of a peptidic antagonist as described above, a nucleic acid encoding thereof, or a nucleic acid vector comprising said nucleic acid for the manufacture of a medicament for the prevention or treatment of a subject suffering of a neurodegenerative disease selected in the group comprising Alzheimer disease, Parkinson disease, central nervous system lesions and demyelination associated pathologies.

In a second preferred embodiment, the present invention relates to the use of a peptidic antagonist as described above, a nucleic acid encoding thereof, or a nucleic acid vector comprising said nucleic acid for the manufacture of a medicament for the prevention or treatment of a subject suffering of a cancer selected in the group comprising lung cancer, breast cancer, mesothelial cancers, carcinoma and glioma In a third preferred embodiment, the present invention relates to the use of a peptidic antagonist as described above, a nucleic acid encoding thereof, or a nucleic acid vector comprising said nucleic acid for the manufacture of a medicament for the prevention or treatment of a subject suffering of a disease associated with abnormal angiogenesis.

Advantageously, said medicament allows the release of a concentration of said peptidic antagonist of more than $10^{-12}$ M, preferably more than $10^{-11}$ M and most preferably more than $10^{-10}$ M.

BRIEF DESCRIPTION OF THE DRAWINGS

FIG. 1 shows the amino acid sequences of the transmembrane domains of mouse neuropilin-1, neuropilin-1, plexin A1, plexin A2, plexin A3, plexin A4, Nr-CAM, L1-CAM, integrin beta 1, and integrin beta 2.

FIG. 2 shows the amino acid sequences of the transmembrane domains of human neuropilin-1, neuropilin-1, plexin A1, plexin A2, plexin A3, plexin A4, Nr-CAM, L1-CAM, integrin beta 1, and integrin beta 2.

FIG. 5(A) shows the morphology of COS-1 cells expressing neuropilin-1 and plexin-A1 in the presence or absence of Sema3A with or without pTM-NRP1 or pTM-NRP1mut. FIG. 5(B) is a graph showing the effects of pTM-NRP1 or pTM-NRP1mut on cellular collapses triggered by Sema 3A.

FIG. 8(A) shows results of a differentiation assay on PC12 cells after incubation with or without NGF (100 ng/mL), Sema 3A, or pTM-NRP1 ($10^{-9}$ M). FIG. 8(B) shows the percentage of differentiation for each of the samples described in FIG. 8(A).

The invention is further illustrated below by the following Examples, which are not intended to limit its scope.

EXAMPLES

1) The Transmembrane Domain of the NRP1 Receptor has a Dimerization Capacity

The ToxLuc System derived from the ToxCat system described in RUSS and ENGELMAN (*Proc. Natl. Acad. Sci. USA*, vol. 96, p: 863-8, 1999) has been used to investigate NRP1 transmembrane domain-mediated dimerization. This system enable to measure transmembrane helix-helix oligomerization in *E. Coli* internal membrane. The dimerization capacity of the transmembrane domain of NRP1 (SEQ ID NO. 1, ILITIIAMSALGVLLGAVCGVVL) has been compared with the one of EGF receptor (SEQ ID NO. 17, SIAT-GMVGALLLLLVVALGIGLFM), Erb-2 protein (SEQ ID NO. 18, SIISAVVGILLVVVLGVVFGILI) and glycophorin A (SEQ ID NO. 19, ITLIIFGVMAGVIGTILLISYGI).

Several constructions were performed, which encodes for the specific fusion proteins. These fusion proteins comprised the N-terminal DNA binding domain of ToxR (a dimerization-dependent transcriptional activator) fused to the transmembrane domain of NRP1, EGF receptor, Erb2 receptor and glycophorin. A respectively, and a monomeric periplasmic anchor (the Maltose Binding Protein: MBP).

The TM sequences of interest were expressed in the bacteria DH5a (MM39) as chimeric proteins flanked by ToxR and by the maltose binding protein (MBP). TM domain-mediated oligomerization results in ToxR-activated expression of a reporter gene encoding chloramphenicol acetyltransferase (CAT) in the original version of the system. For convenience, we used conventional molecular biology methods to replace the initial CAT gene by that of luciferase. Synthetic TM sequences corresponding to neuropilin, EGF receptor and wild-type erbB2 were cloned into the new plasmid as NheI/DpnII fragments. Chimeras with TM sequences derived from glycophorin A or its G83I mutant (RUSS and ENGELMAN, Proc. Natl. Acad. Sci. USA., vol. 96(3), p: 863-8, 1999) were used as controls. Luciferase assay was performed using the ROCHE assay kit according to the manufacturer instructions, and a Berthold Microlumat plate luminometer.

Figure 3:
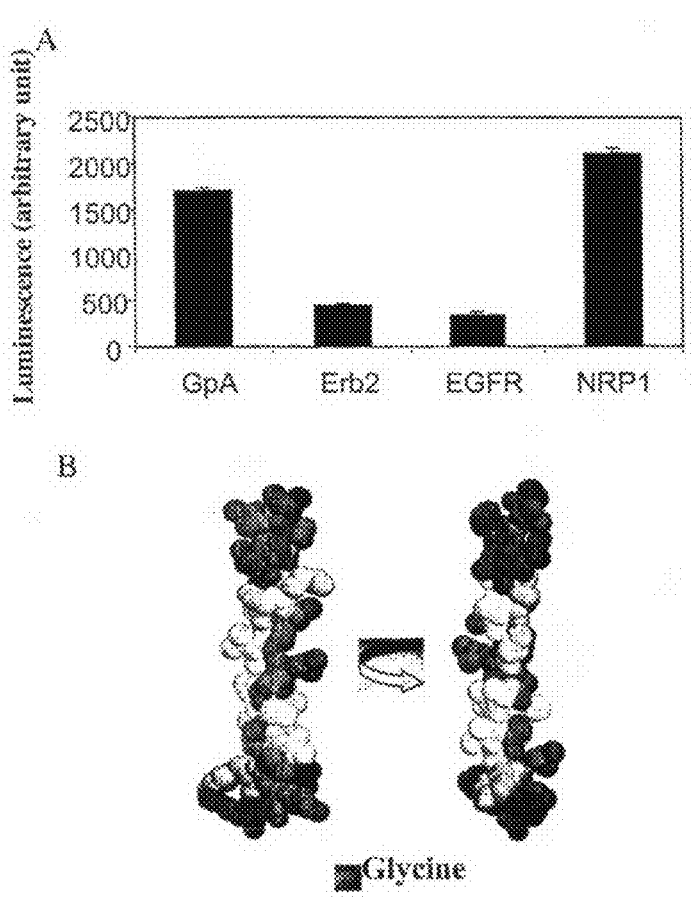
FIG. 3(A) is a graph showing the dimerization capacity of the transmembrane domain of neuropilin-1 compared to that of the transmembrane domain of EGF receptor, Erb-2 protein and glycophorin A measured as described in Example 1.
FIG. 3(B) is a model showing the existence of a spatial compact organization of the transmembrane domain of neuropilin-1 presenting inter-helices interactions in favor of dimer formation.

The results are shown in FIG. 3A for the different constructions.

The results show that the bacteria transformed with the construct containing the transmembrane domain of NRP1 show a significantly higher luciferase luminescence than those containing the transmembrane domain of Erb-2 (4.7 factor) or EGFR (6.1 factor) and slightly superior to those containing the one of glycophorin-A (1.2 factor). Interestingly, we confirmed the dimerization capacity of NRP1 TM domain by a 3 dimensional model of TM-NRP1 obtained with the SwissPdbViewer software on the basis of the RMN structure of the glycophorin-A. This theoretical approach, although being minimalist, confirmed the existence of a spatial compact organization of the TM-NRP1 presenting inter-helices interactions in favor of dimer formation (FIG. 3B).

In conclusion, the transmembrane domain of NRP1 is able to induce the dimerization with a efficiency stronger than the dimerization capacity of GpA transmembrane domain.

2) The Transmembrane Domain Peptide of the NRP1 Receptor Inhibits Cortical Axons Collapses Triggered by Sema3A The inhibitory axon growth property of Sema 3A is supposed to be linked to its induction capacity of growth cone collapses. To investigate the effect of the pTM-NRP1 peptide on the Sema 3A functional properties, the growth of cortical neurons was analyzed in the presence or not of Sema 3A and of pTM-NRP1 or pTM-NRP1$^{mut}$ (NRP1 TM with a triple G→V mutation) peptides.

Laminine/Poly-L-Lysine substrates have been made by adding 980 μL of Gey's balanced salt solution (GBSS, SIGMA) to 10 μL laminine (1 mg/ml, SIGMA) and to 10 μL poly-L-Lysine (10 mg/ml, SIGMA). Sterile coverslips have been placed in a big dish and added with substrate (100 μL). Then, 'sandwiches' have been prepared by covering each coverslip with a second one. After an incubation for at least 30 min at 37° C. under 5% $CO_2$ in air, 'sandwiches' have been opened and each coverslip has been rinsed with deionized water. Explants have been cultured on dried coverslips.

Neocortex fragments prepared from E15 mouse embryos (E1 determined as the first day of embryonic development by detection of vaginal plug) have been transferred on a tissue chopper disk. Tissue have been cut into 200×200 μm by rotating the disk by 90° after the first cut. Cortex cubes have been collected with a spatula and put into culture medium in a Petri dish. Two coverslips with substrate have been placed in a small Petri dish (50 mm diameter, FALCON). After adding 750 μl of culture medium, the coverslips should stay in the incubator for at least 10 minutes. Using a dissecting microscope, forty to fifty cortical explants have been collected in 20 μl culture medium and carefully placed onto the coverslips. After 15 min at room temperature, most explants have adhered to their substrate. 2250 μl of culture medium have been slowly added to each dish. Then, explants cultures have been kept at 37° C. under 5% $CO_2$ in air.

A radial outgrowth could be seen after 18-24 h in culture, and individual fibres and growth cones could have therefore been analyzed. Products tested on growth cones have been directly added in culture medium for 2 h:

purified Sema3A (100 ng/ml) prepared from conditioned medium of HEK293 cells stably expressing Sema3A. The purification was performed by using the anti-Flag system, SIGMA)

pTM-NRP1 ($10^{-8}$, $10^{-9}$, $10^{-10}$ and $10^{-11}$ M), $10^{-8}$M mpTM-NRP1, $10^{-8}$M pTM-ErbB2w (SEQ ID NO. 18).

After incubation, 4% formaldehyde has been directly added in culture medium (v/v) for 15min. Then the solution has been removed and replaced by 4% formaldehyde for 15 min.

Figure 4:
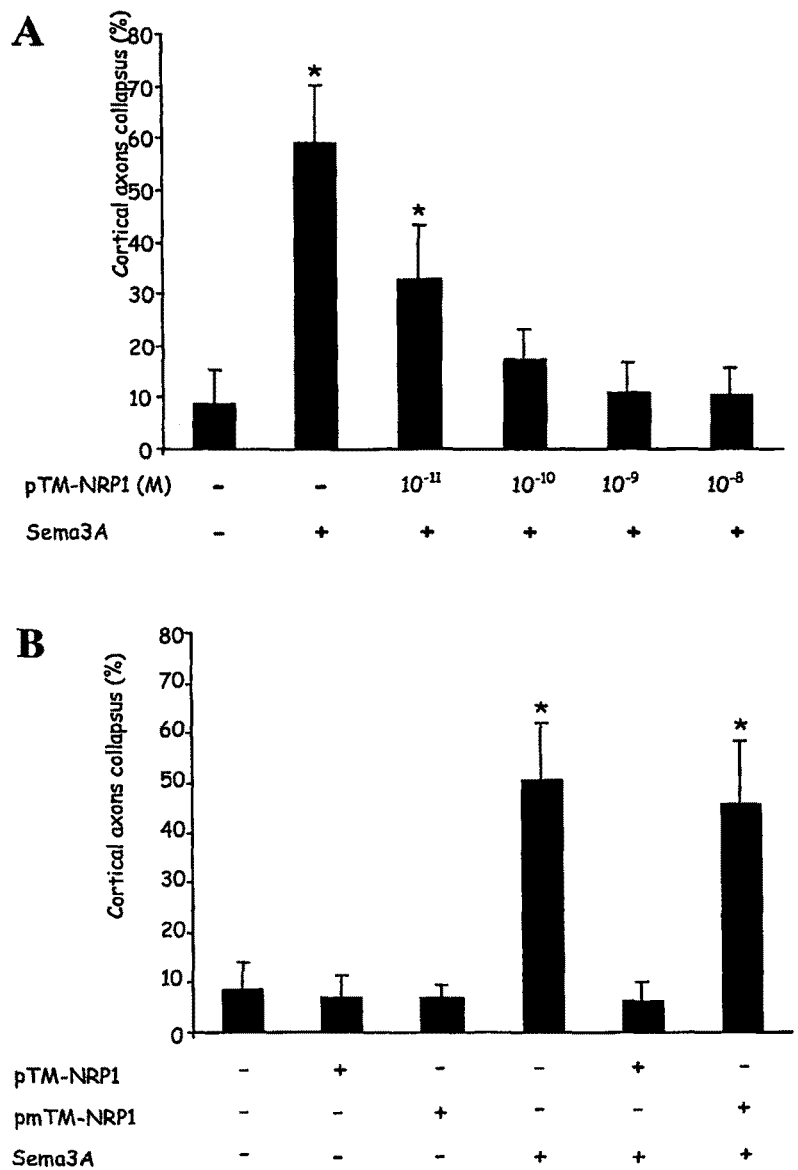
FIG. 4(A) is a graph showing the effect of increasing the concentration of the transmembrane domain of neuropilin-1 (pTM-NRP1) on cortical axons collapses triggered by Sema3A.
FIG. 4(B) is a graph showing the effect of pTM-NRP1 ($10^{-8}$M) or of the transmembrane domain of neuropilin containing a triple G→V mutation (pTM-NRP1$^{mut}$) ($10^{-8}$M) on cortical axons collapses triggered by Sema3A.

The FIG. 4A shows the effect of increasing concentrations of pTM-NRP1 peptide ($10^{-8}$, $10^{-9}$, $10^{-10}$ and $10^{-11}$M) on cortical axons collapses triggered by Sema3A.

The FIG. 4B shows the effect of pTM-NRP1 or pTM-NRP1$^{mut}$ peptide ($10^{-8}$ M) on cortical axons collapses triggered by Sema3A.

The results show that more than 50% of collapsed cortical axons were observed in Sema3A-treated cells, whereas less than 10% of the cortical axons presented collapsed morphology in control conditions (FIG. 4A). Furthermore, the addition of increasing concentrations of the wild type pTM-NRP1 peptide suppressed the collapsed effect of Sema3A on cortical axons in a dose dependant manner with an IC50 of nearly $10^{-11}$ M.

In contrast, the addition of the pTM-NRP1$^{mut}$ peptide did not block the cortical axons collapses triggered by Sema3A (FIG. 4B).

Control experiment with peptide dilution buffer and with ErbB2 peptide, which contains a GxxxG motif, show no effect on the collapsing effect of Sema 3A.

These results demonstrate that the addition of a synthetic peptide mimicking the transmembrane domain of NRP1 abolishes the effects of Sema3A on cortical axons, inhibiting cortical axons collapses. Moreover, this biological activity is associated with the GxxxG motif and is specific from the pTM-NRP1 peptide.

3) The Transmembrane Domain Peptide of the NRP1 Receptor Inhibits COS Cellular Collapses Triggered by Sema3A The COS cells do not express semaphorin receptors and are therefore naturally not sensitive to these guidance signals. Nevertheless, the artificial expression of NRP1 and Plexin-A1 in COS cells allows Sema 3A to trigger cellular collapses. To investigate the effect of the pTM-NRP1 peptide on the Sema3A functional properties, the shape of COS cells expressing NRP1 and Plexin-A1 was analyzed in the presence or not of Sema 3A and of pTM-NRP1 or pTM-NRP1$^{mut}$ peptide.

COS-1 cells have been transfected by 1 µg of pBK-CMV (STRATAGENE) plasmids containing NRP1 and plexin-A1 coding sequences (provided by Pr. PUSCHEL; MUNSTER Universitat, Germany) with LIPOFECTAMINE 2000 (IN VITROGEN) according to the manufacturer's instructions in 6-well plates. Stably COS-1 transfected cells have been selected with 0.7% geneticine. Stably transfected COS-1 cells have been cultured on 12-well plates with previously poly-L-lysine-coated glass coverslips. Cells have been then incubated 1 hour with pTM-NRP1 or pTM-NRP1$^{mut}$ peptide ($10^{-9}$M) at 37° C. The culture medium has been then removed and replaced by conditioned medium of HEK cells stably transfected or not with a construction expressing Sema 3A (100 µl/ml D-MEM) for 4 hours at 37° C. Finally, cells have been fixed with 2% formaldehyde for 30 minutes followed by 15 minutes in formaldehyde 4%. For each condition tested, about 400 cells have been analyzed.

The FIG. 5A show the morphology of COS-1 cells expressing NRP1 and Plexin-A1 in the presence or absence of Sema 3A with or without pTM-NRP1 or pTM-NRP1$^{mut}$ peptide. The FIG. 5B show the effect of pTM-NRP1 or pTM-NRP1$^{mut}$ peptide on the cellular collapses triggered by Sema 3A (*: p<0.001).

The results show that more than 50% of collapsed cells were observed in Sema 3A-treated cells, whereas less than 10% of the cells presented collapsed morphology in control conditions (FIG. 5B). Furthermore, the addition of $10^{-9}$ M of pTM-NRP1 peptide completely abolished the collapsing effect of Sema3A on COS-1 cells. In contrast, the addition of $10^{-9}$ M of the pTM-NRP1$^{mut}$ peptide, which has a mutated GxxxG motif, did not block the cellular collapses triggered by Sema 3A.

These results demonstrate that the addition of a synthetic peptide mimicking the transmembrane domain of NRP1 abolishes the cellular collapsing effect of Sema 3A with its GxxxG motif.

To address the mechanism by which pTM-NRP1 blocked Sema3A signaling we performed binding assays.

NRP1 expressing COS cells were incubated with AP-Sema3A, a fusion protein of Sema3A and the secreted alkaline phosphatase (BAGNARD et al., 1998).

Wild-type COS cells or NRP1-expressing COS cells (COS-NRP1) were cultured on 12-wells plates on poly-L-lysine-coated glass coverslips (0.005 mg/ml). After one-hour incubation with pTM-NRP1 or pTM-NRP1$^{mut}$ ($10^{-9}$M) in serum-free medium at 37° C., the culture medium was replaced by conditioned medium containing alkaline phosphatase-coupled Sema3A (AP-Sema3A; BAGNARD et al., 1998) obtained from AP-Sema3A stably expressing HEK cells for 90 mn. Conditioned medium without semaphorin served as a control (obtained from non-transfected HEK). Cells were washed three times with PBS and fixed in 4% formaldehyde before transfer in a new dish. After three washes in PBS, the plate was warmed for 50 mn at 65° C. Cells were subsequently incubated with 1 ml of alkaline phosphatase substrate (NBT/BCIP, SIGMA) in the dark. After 45 mn, substrate was removed and glass coverslips were rinsed. Pictures were acquired with a conventional microscope and analyzed with AxioVision LE Zeiss software. For each condition tested, about 60 cells were analyzed to determine binding levels as a function of optical density. Statistical analysis was performed by using a Student's t test.

Figure 6:
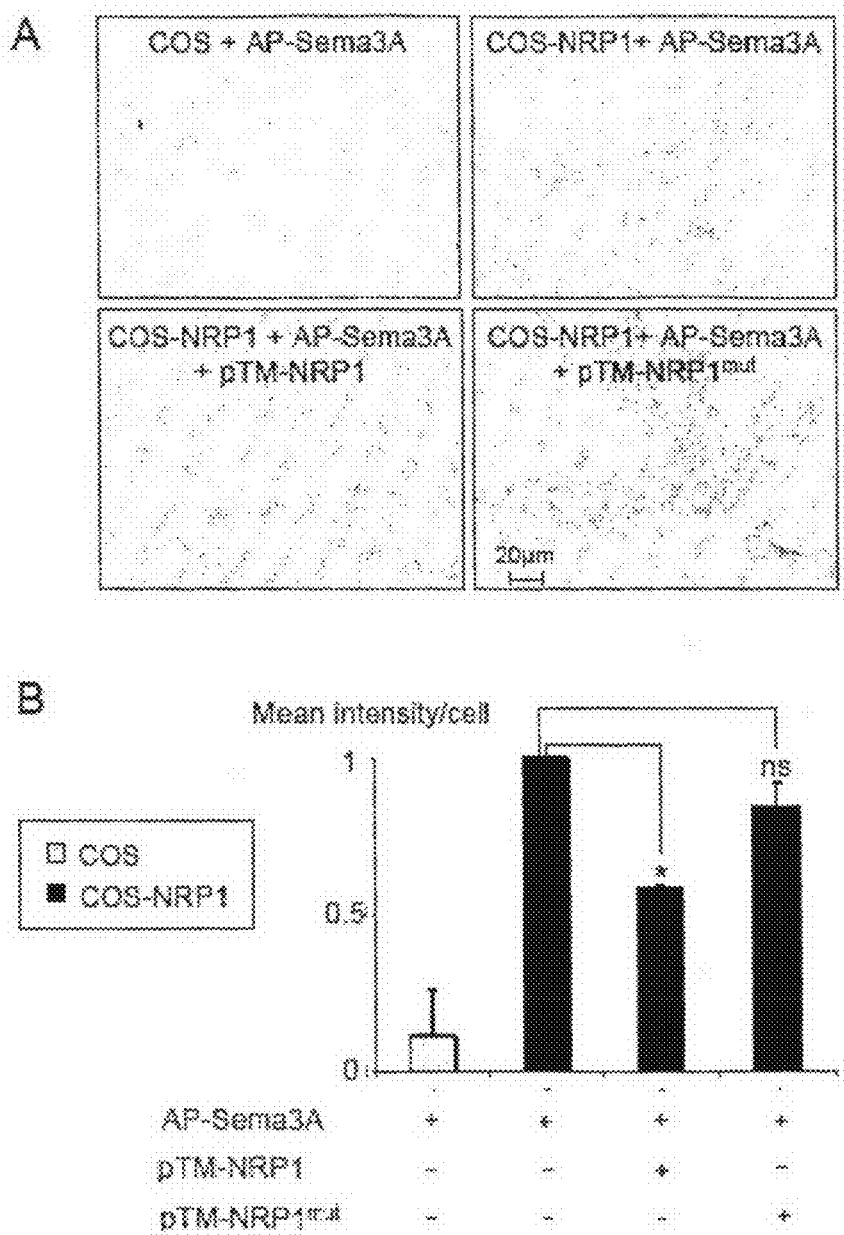
FIG. 6(A) shows wild type COS cells (control) and NRP1-expressing COS cells (COS-NRP1) after incubation with AP-Sema3A with or without pTM-NRP1 or pTM-NRP1$^{mut}$.
FIG. 6(B) shows the mean intensity of optical density per cell measured for the samples described in FIG. 6(A).

The FIG. 6A shows the Wild type COS cells (control) or NRP1 expressing COS cells (COS-NRP1) after incubation with AP-Sema3A with or without pTM-NRP1 or pTM-NRP1$^{mut}$.

The FIG. 6B shows the mean intensity of optical density per cell for the previous tested conditions.

The results show that the binding of AP-Sema3A was significantly reduced by addition of pTM-NRP1 (FIGS. 6A and B). Strikingly, the addition of pTM-NRP1$^{mut}$ did not block AP-Sema3A binding to COS cells.

These results demonstrate that the GxxxGxxxG domain of NRP1 TM appeared crucial to trigger Sema3A binding and subsequent inhibitory effect.

4) Mutation of the TM Domain of NRP1 Disrupts Receptor Function

In order to confirm the pivotal role of the GxxxGxxxG motif, mutations were introduced into the TM domain of a full length NRP1 to replace all three glycines residues by valines (NRP1$^{mut}$) as in the mutated peptide.

A plasmid encoding for a NRP1 protein with the triple (G→V) mutation in the transmembrane region was transfected in COS cells as described previously. Then, binding experiments were conducted in COS cells expressing this mutated form of NRP1 as previously.

Figure 7:
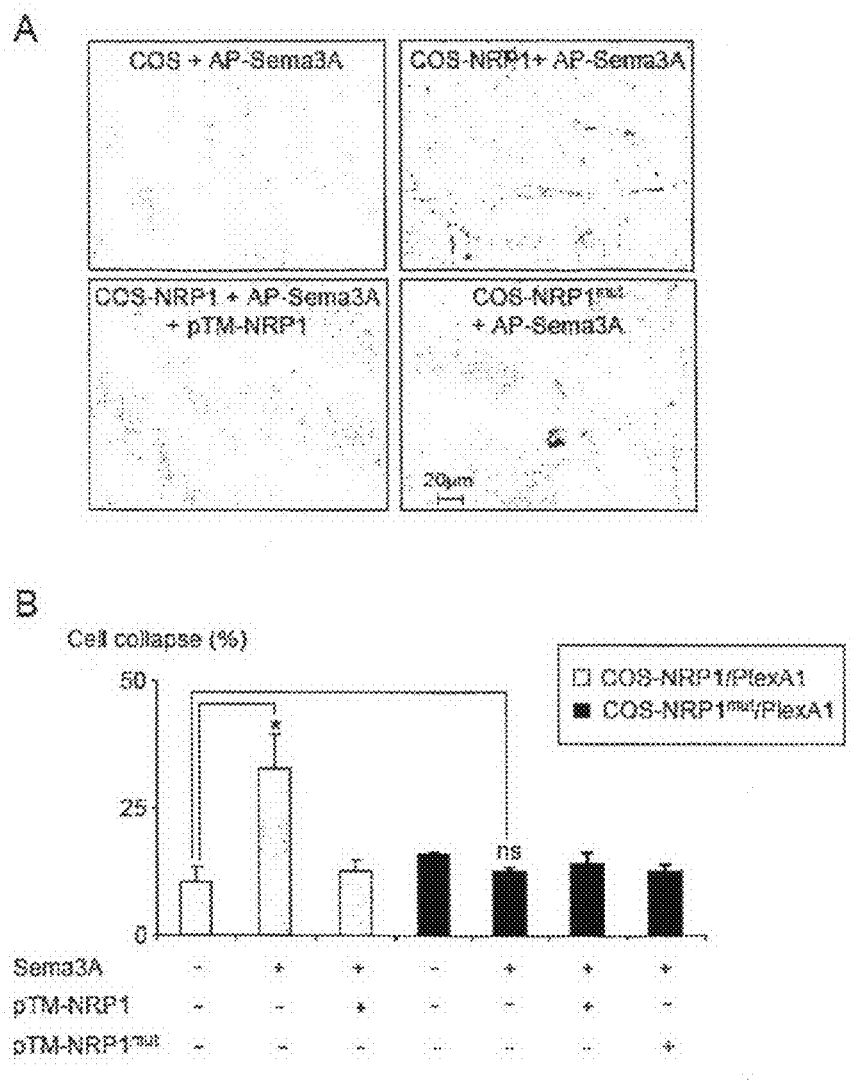
FIG. 7(A) shows wild type COS cells (control), NRP1-expressing COS cells (COS-NRP1), and COS cells expressing neuropilin with a triple G→V mutation (COS-NRP1$^{mut}$) after incubation with AP-SemaA3 with or without pTM-NRP1.
FIG. 7(B) shows the mean intensity of optical density per cell measured for the samples described in FIG. 7(A).

The FIG. 7A shows the Wild type COS cells (control), NRP1 expressing COS cells (COS-NRP1), or NRP1 with the triple (G→V) mutation expressing COS cells (COS-NRP1$^{mut}$) after incubation with AP-Sema3A with or without pTM-NRP1.

The FIG. 7B shows the mean intensity of optical density per cell for the previous tested conditions.

The results show that, while significant binding was observed in COS cells expressing the wild type NRP1 very low if any binding of AP-Sema3A was detected in cells expressing NRP1$^{mut}$ (FIG. 7A). The strong reduction, of binding was similar to the one obtained in the presence of the pTM-NRP1. Strikingly, when this NRP1 mutant (NRP1$^{mut}$) was expressed in COS cells together with PlexA1, Sema3A was no longer able to induce a cell collapse (FIG. 7B). This further confirmed the importance of the GxxxGxxxG motif of NRP1 TM domain for the formation of a functional Sema3A receptor.

5) Synthetic Peptides Mimicking TM-NRP1 Alter the Formation of the Semaphorin Receptor Complex To further investigate the biochemical consequence of the TM-NRP1 in terms of receptor complex formation, we analyzed the formation of complexes in the PC12 neuronal cells model. Interestingly, Sema3A has been shown to promote the growth of neurites in these cells through a NGF-independent pathway (SCHWAMBORN et al., J. Biol. Chem., vol. 279 (30), p: 30923-6, 2004).

PC12 (ATCC: CRL-1721) were grown in D-MEM medium with 4.5 g of glucose/L (GIBCO), 5% FVS, 10% horse serum, glutamine 580 mg/L and antibiotics. For functional assays, PC12 were cultured on 12-wells plates with previously poly-L-lysine-coated glass coverslips. PC12 cells were incubated 1 h with or without pTM-NRP1 peptide ($10^{-9}$M) at 37° C. Culture medium was removed and replaced by NGF-containing (100 ng/mL; GIBCO) serum free medium or by conditioned medium obtained from HEK293 cells stably expressing Sema3A or non-transfected cells (control, see BAGNARD et al., 1998 for details) for 12 h at 37° C.

Cells were fixed with 2% formaldehyde for 30 mn followed by 15 mn in 4% formaldehyde. For each condition tested, around 400 cells were analyzed to evaluate neuritic outgrowth (Statistical analyses were made by using $\chi^2$ test).

The FIG. 8A shows the result of the differentiation assay of PC12 cells after their incubation with or without NGF (100 ng/ml), Sema 3A, pTM-NRP1 ($10^{-9}$ M).

The FIG. 8B shows the percentage of differentiated cells for each condition.

The results show that the addition of NGF or Sema3A induced PC12 cell differentiation without synergistic effects (FIGS. 8A and 8B). Moreover, when experiments were done in the presence of pTM-NRP1, the Sema3A induced neurite growth promotion was significantly reduced while the NGF effect was preserved. This demonstrated that the addition of the peptide specifically blocked the activation of Sema3A-dependent pathways without affecting other signaling pathways.

6) The Transmembrane Domain Peptide of the NRP1 Receptor Antagonizes the Binding of the Ligand Sema3A to its Receptor NRP1

In order to investigate the NRP1 transmembrane domain role in the linkage NRP1-class III semaphorins, the binding of the ligand Sema3A to its receptor NRP1 on glioma cells was measured in the presence or not of the transmembrane domain peptide of NRP1 (pTM-NRP1 peptide; SEQ ID NO. 1) or of a mutated peptide (mpTM-NRP1; SEQ ID NO. 20, ILITIIAMSAL$\underline{V}$VLL$\underline{V}$AVC$\underline{V}$VVLYRKR). These pTM-NRP1 Peptides have been synthesized by automatic peptidic synthesis (Fmoc chemistry, APPLIED SYSTEM), and analyzed by mass spectrometry. Peptides purity has been estimated by RP-HPLC (BECKMAN) as higher than 90%.

Rat C6 glioma cells, which express semaphorin receptors, has been used to determine the binding capacity of AP-Sema3A, a secreted alkaline phosphatase version of Sema 3A (ADAMS et al., 1997, BAGNARD et al., 1998). These cells were grown and plated in MEM medium (GIBCO) with 10% foetal calf serum (PERBIO), glutamine 0.5 mM (GIBCO) and antibiotics: 100 U/ml penicillin and 100 µg/ml streptomycin (SIGMA).

C6 Cells were cultured in 96-well plates and incubated with or without freshly diluted pTM-NRP1 or pTM-NRP1$^{mut}$ peptides ($10^{-12}$ M to $10^{-10}$ M) for 1 hour at 37° C. The culture medium has been then replaced by conditioned medium of HEK cells stably transfected with a construction expressing AP-Sema 3A (ADAMS et al., *EMBO J.*, vol. 16(20), p: 6077-86, 1997; BAGNARD et al., 1998). Conditioned medium from HEK non transfected cells has been used as an internal control. The pTM-NRP1 Peptide has been synthesized by automatic peptidic synthesis (Fmoc chemistry, APPLIED SYSTEM), and analyzed by mass spectrometry. Peptides purity has been estimated by RP-HPLC (BECKMAN) as higher than 90%, the cells have been washed with PBS and incubated with 50 µl of alkaline phosphatase luminescent substrate (AMERSHAM). The luminescence has been read after 15 minutes with MICROLUMAT PLUS system (BERTHOLD TECHNOLOGIES) according to the manufacturer's instructions. Experiments were done 4 times for each peptide.

Figure 9:
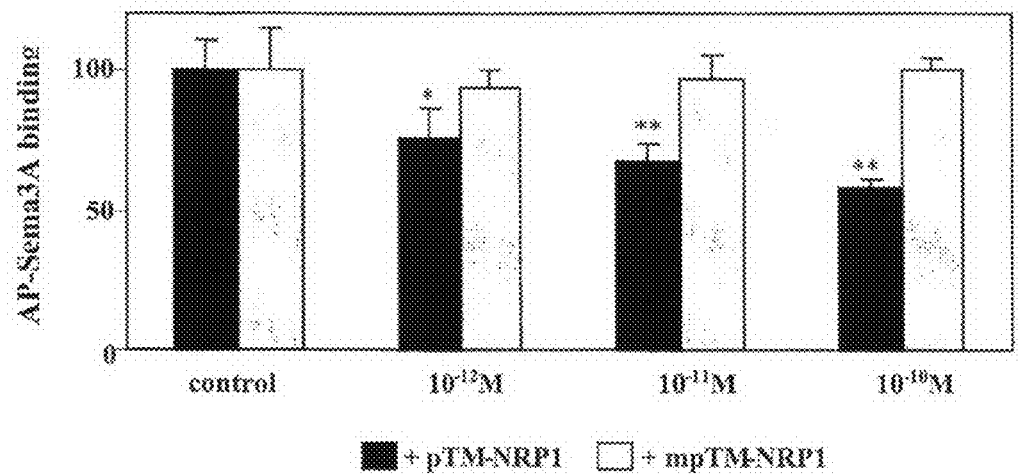
FIG. 9 is a graph showing the binding of AP-Sema3A to its receptor in the presence of pTM-NRP1 peptide (black bars) or mutated pTM-NRP1 (grey bars) (*: $p<0.005$; **: $p<0.01$, Student test).

The results for the AP-Sema 3A binding to its receptor in the presence of pTM-NRP1 peptide (black bar) or mutated (grey bar) are shown in FIG. 9 (*: p<0.005; **: p<0.01, Student t test).

The results show that the binding of AP-Sema3A to its receptor NRP1 on C6 cells was blocked in a dose dependent manner by addition of increasing concentrations of the wild type pTM-NRP1 peptide. In presence of $10^{-10}$M of the wild type pTM-NRP1 peptide, the binding of AP-Sema3A to NRP1 decreased from about 50% compared to the absence of peptide. In contrast to the wild type pTM-NRP1 peptide, addition of pTM-NRP1$^{mut}$ peptide did not block the binding of AP-Sema3A to NRP1.

As a result, the binding of Sema3A to its receptor NRP1 involves the transmembrane domain of NRP1 and requires the integrity of the double GxxxG motif.

7) The Transmembrane Domain Peptide of the NRP1 Receptor Alters the Formation of the Semaphorin Receptor Complex To further investigate the role of the transmembrane domain of the NRP1 receptor in the formation of the NRP1 receptor complex, the formation of NRP1 complexes has been determined on C6 cells expressing NRP1 and plexin-A1 in the presence or not of the transmembrane domain peptide of NRP1 (pTM-NRP1 peptide) and of the ligand Sema3A.

C6 cells expressing NRP1 and Plexin-A1 were incubated or not with the pTM-NRP1 peptide ($10^{-9}$ M) for 1 h. The culture medium has been then replaced of HER cells stably transfected or not with a construction expressing Sema 3A. Confluent C6 have been harvested with 10 mM EDTA and centrifuged. The pellet has been washed in PBS and then diluted in lysis buffer (Tris-HCL/NaCl; 50/150; pH 8.0) with 0.1% SDS, 1 mM EDTA, 1% NP-40, 0.5% DOC, 2 mM vanadate and proteases inhibitors without SDS (PIERCE). After solubilization for 1 h at 4° C., protein amount is estimated by bicinchoninic acid method (BCA Protein Assay, PIERCE).

Sucrose density gradient sedimentation experiments were based on a step gradient containing 25%, 17%, 10% and 3% sucrose. Solutions have been made from Hepes/NaCl buffer (30/30, pH 7.6, 0.12% triton) and Hepes/NaCl buffer with 1M sucrose. These solutions were successively loaded in order to form a linear gradient (LERAY et al., Arch Biochem Biophys., 1992).

The cell lysates were placed on the gradient in an ultracentrifuge tube and centrifuged at 100 000 g for 1 hour with a TL-100 ultracentrifuge (BECKMAN) and the fractions have been collected from the bottom (13 drops/fraction).

According to LAEMMLI's method, an equivalent volume of loading buffer has been added to samples (62.5 mM Tris-HCL pH 6.8, 10% glycerol, 2% SDS, DTT, bromophenol blue) and these have been boiled for 10 minutes. Then samples have been subjected to SDS-PAGE on acrylamide gel (5-20%) at constant voltage and temperature in adequate buffer (0.025M Tris, 0.192M Glycine pH 8.3, 0.01% SDS). Proteins have been then transferred to methanol-activated polyvinyldiene difluoride (PVDF) membrane at 4° C. for 3 hours in a buffer containing 20% ethanol, 0.025M Tris, 0.192M Glycine pH 8.3, and 0.01% SDS. Finally, the PVDF membrane has been blocked for 1 hour with PBS/BSA 5%.

The membrane has been then incubated 2 hours with polyclonal anti-NRP1 at a 1:1000 dilution (ONCOGENE). The membrane has been washed three times in PBS/0.2% TWEEN 20 and incubated with the secondary antibody (A/G protein, PIERCE, 1:100 000 or horseradish peroxydase-linked anti-rabbit IgG, AMERSHAM, 1:500). Immunoreactivity has been then detected with an enhanced chemoluminescence western blot detection system (PIERCE) according to the manufacturer's instructions.

Figure 10:
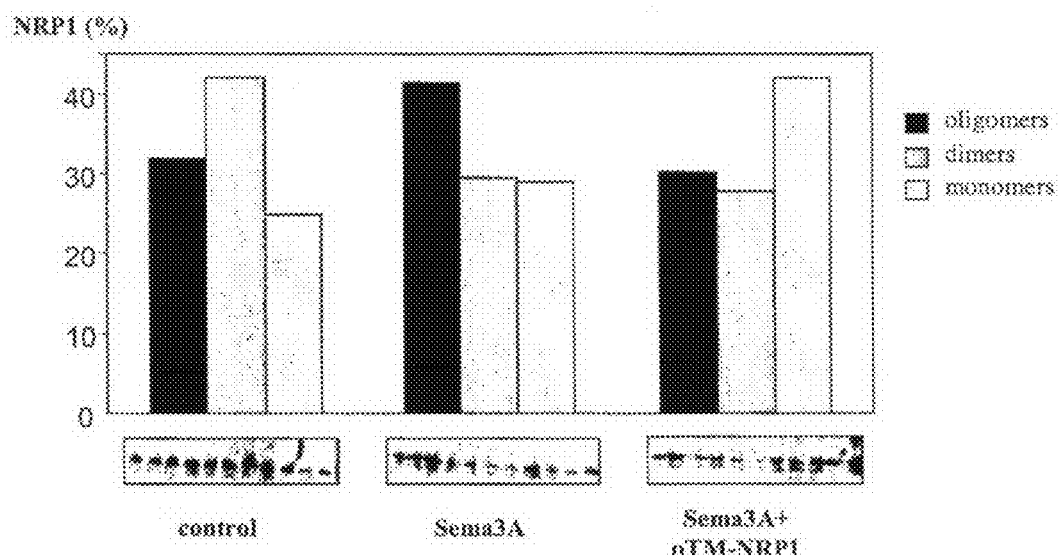
FIG. 10 is a graph showing the formation of NRP1 complexes in C6 cells expressing NRP1 and plexin-A1 in the presence or in the absence of the transmembrane domain of NRP1 (pTM-NRP1) and of the ligand Sema3A.

The results are shown in FIG. 10. NRP1 percentage in each fraction was calculated from total revealed NRP1. In this figure, heavy fractions of the sucrose gradient containing oligomers including Plexin-A1 correspond to black bars, medium fractions containing NRP1 dimers correspond to grey bars, and light fractions were almost composed of NRP1 monomers correspond to empty bars.

The results show that in the absence of the ligand Sema 3A, NRP1 was predominantly detected in the medium fractions of the gradient sucrose. Thus, the NRP1 dimers represented the major forms of NRP1 receptor in the absence of its ligand Sema3A.

In contrast, in presence of Sema3A, NRP1 receptors were predominantly present as oligomeric forms including plexin-A1 in the heavy fractions.

The addition of the pTM-NRP1 peptide in the presence of Sema 3A modified the distribution of NRP1, which was mainly detected in the light fractions corresponding to the migration level of NRP1 monomers. Thus, the oligomerization of NRP1 was inhibited by the presence of the pTM-NRP1 peptide. Hence, the transmembrane domain of NRP1 is involved in the formation of NRP1 receptor complex. Consequently, the decrease of Sema 3A binding observed in FIG. 3 in the presence of the pTM-NRP1 peptide could be correlated to the inhibition of the NRP1 oligomerization.

8) Functional Implication of pTM-NRP1-Dependent Inactivation of NRP1 during Tumour Cell Migration The rat C6 glioma cell line, which is a good model of human glioma (DAI and HOLLAND, Biochim. Biophys. Acta, vol. 1551, p: M19-27, 2001), has been used to investigate how the blockade of NRP1 by using our peptidic strategy (pTM-NRP1) may interfere with cell migration and dissemination.

C6 cells (ATCC CCL-107) were stained using PKH26 (Sigma). Cells were incubated with peptides (pTM-NRP1 $10^{-8}$M or mutated pTM-NRP1 $10^{-8}$M) prior to injections for at least 2 h on ice in culture medium (composed of MEM with 5000 u/ml penicillin, 5 mg/ml streptomycin, 200 mM L-glutamine and 10% fetal calf serum). Injections of $10^6$ cells were performed using a stereotaxic frame according to the following coordinates: antero-posterior, +1.6 mm relative to Bregma; L, +2 mm; H, +5 mm relative to the cortical surface.

All injections were performed in the left striatum.

Following a survival period of 8 days, the animals (3 groups of 4 rats) were killed by a lethal intra-peritoneal injection of pentobarbital before trans-cardiac perfusion with a pre-rinse of 100 ml PBS followed by 500 ml of 2% formaldehyde. The brains were post-fixed during 2 hours at 4° C. and sagittal sections (70 µm) were prepared on a vibratome.

Figure 11:
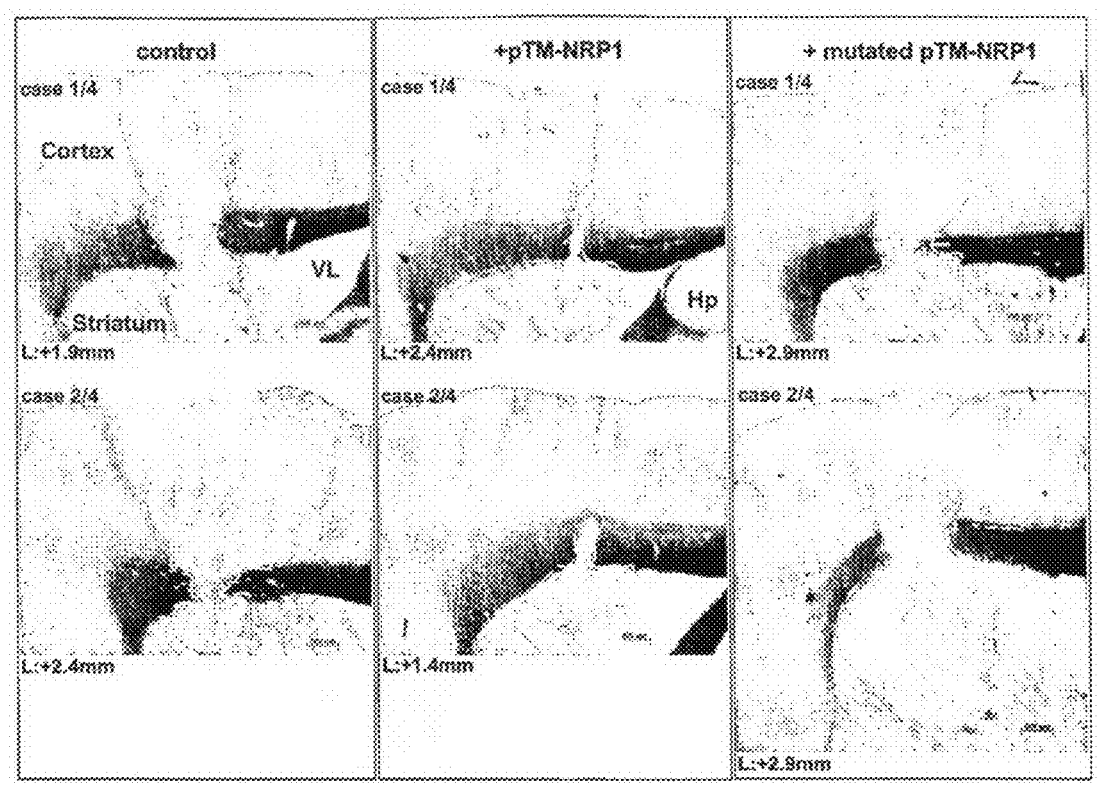
FIG. 11 shows several mouse brain sections after injection into the brain of C6 cells with or without pTM-NRP1 or pTM-NRP1$^{mut}$ peptides. The positions of the tumor, cortex, striatum, corpus callosum (cc), hippocampus (Hp) and lateral ventricle (VL) are depicted.

One group of sections were mounted in PBS-glycerol (v/v) for microscopic observation, and another one was treated for immunostaining of CD34. Sections were first incubated in PBS containing 5% calf normal serum for 15 minutes at room temperature to block non-specific binding sites. A second incubation was performed for 1 hour at room temperature and then overnight at 4° C. with a mouse anti-CD34 (1:200). The sections were washed six times during 5 minutes in PBS, and were then incubated with a goat anti-mouse antibody bound to Alexa-488 (1:500; INTERCHIM) for 3 hours at room temperature. Sections were washed six times during 5 minutes in PBS and were finally mounted in PBS-Glycerol (v/v) before microscopic analysis The FIG. 11 shows the mouse brain sections after the brain injection of C6 cells with or without pTM-NRP1 or pTM-NRP1$^{mut}$ peptides. The positions of the Tumour, cortex, striatum, corpus callosum (cc), hippocampus (Hp) and lateral ventricle (VL) are depicted on microphotographs.

Figure 12:
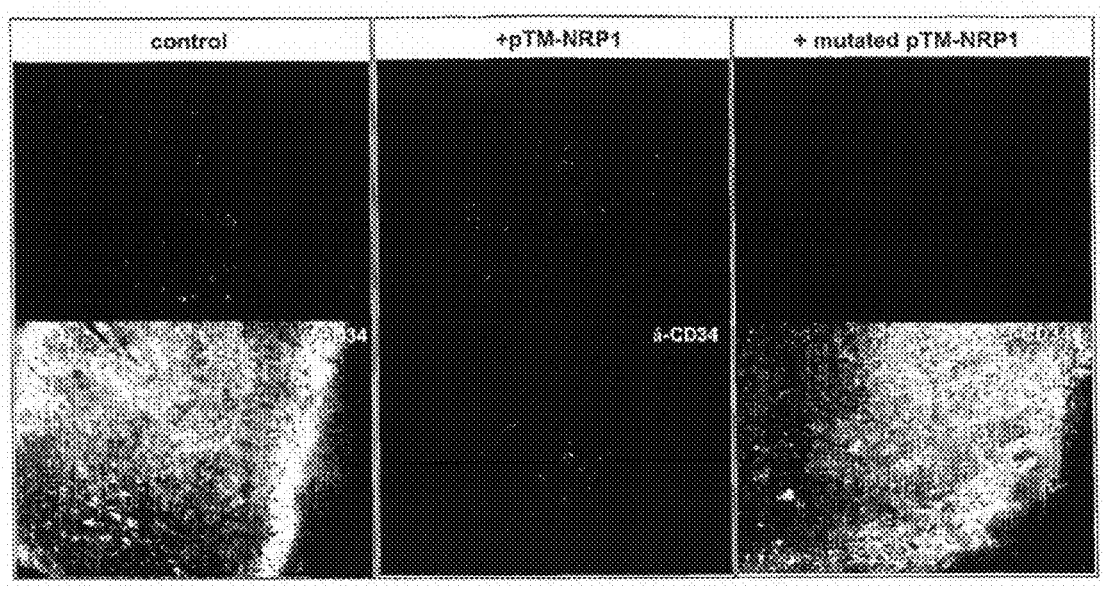
FIG. 12 shows mouse brain sections after injection into the brain of C6 cells with or without pTM-NRP1 or pTM-NPR1$^{mut}$ peptides after immunostaining of CD34.

The FIG. 12 shows the mouse brain sections after the brain injection of C6 cells with or without pTM-NRP1 or pTM-NRP1$^{mut}$ peptides after an immunostaining of CD34.

The results show that, in control conditions, tumours developed in the striatum and reached the corpus callosum and the cortical plate (FIG. 11, n=4). Strikingly, when cells were treated with pTM-NRP1 prior to injection, we observed a strong reduction of the tumour size at 8 days. (n=4). As expected, C6 cells treated with mutated pTM-NRP1 induced tumours similar to those observed with non-treated, cells (n=4). Thus, the addition of pTM-NRP1 inhibits the development of C6 glioma.

The results show also that the reduction of tumour size in the presence of pTM-NRP1 was accompanied by a strong reduction of the immunoreactivity for CD34, a marker of neoangiogenesis (FIG. 12). This suggested that pTM-NRP1 exerts its anti-tumour effect by blocking VEGF signalling.

9) pTM-NRP1 can Antagonize VEGF Signalling In Vitro

NRP1 is a receptor of VEGF (NEUFELD et al., Adv. Exp. Med. Biol., vol. 515, p: 81-90, 2002). We therefore verified that pTM-NRP1 can antagonize VEGF signalling in C6 cells. To this end, C6 tumour cell aggregates prepared as previously described (see BAGNARD et al., 1998; and NASARRE et al., Neoplasia, vol. 7, p: 180-189, 2005) were grown in the 3D matrix (plasma clot) and treated with VEGF165.

Figure 13:
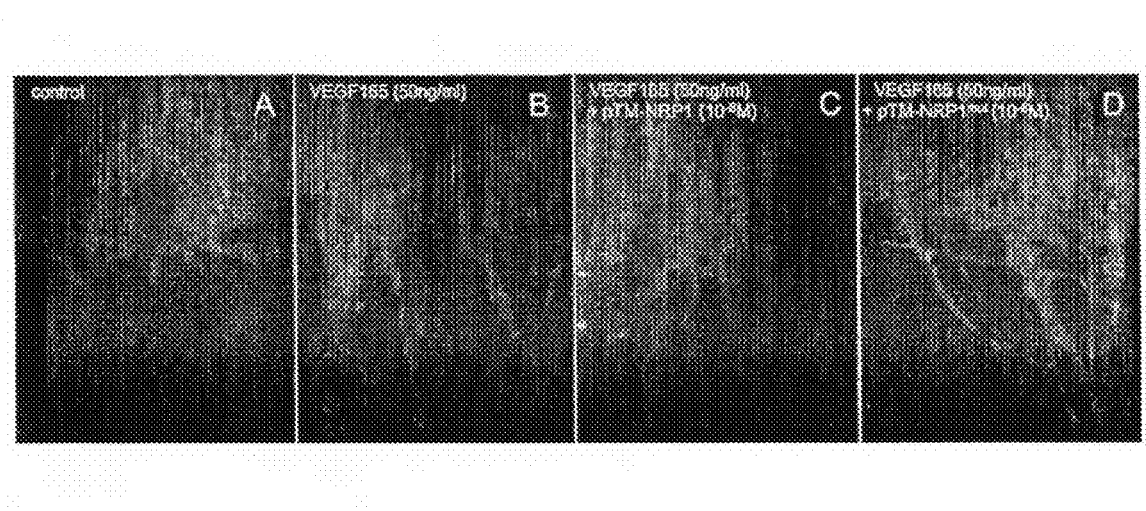
FIG. 13 shows tumor cell aggregates in the presence or not of VEGF$_{165}$ (50 ng/ml), pTM-NRP1 or pTM-NRP1$^{mut}$ ($10^{-8}$ M).

The FIG. 13 shows representative tumour cell aggregates with or without the addition of VEGF165 (50 ng/ml), pTM-NRP1 or pTMNRP1$^{mut}$ ($10^{-8}$ M).

The results show that the addition of 50 ng/ml VEGF165 induced C6 cells migration out of the aggregates and formation of migration chains (FIG. 13). Strikingly, the addition of pTM-NRP1 suppressed VEGF165-dependent C6 cells migration. The addition of mutated pTM-NRP1 was not able to block VEGF165-induced C6 cell migration. These results suggest that pTM-NRP1 is able to block VEGF165 signalling in C6 cells thereby reducing tumour cells dissemination.

Finally, these results strongly suggest that that pTM-NRP1 can be used to block NRP1 signalling in the context of tumorigenesis. This is related to the role of NRP1 during tumour cell migration and survival through VEGF-dependent mechanisms. We propose that the blockade of NRP1 using pTM-NRP1 has a therapeutic outcome for any tumour whose survival, growth and or dissemination requires a NRP1-dependent signalling cascade.

The invention claimed is:

1. A method for the treatment of a subject suffering from a disease associated with class III semaphorins/neuropilins complexes signal transduction pathways, comprising administering to the subject a pharmaceutical composition comprising a peptidic antagonist of class III semaphorins/neuropilins complexes, the peptidic antagonist
   consisting of a transmembrane domain of a protein selected from the group consisting of neuropilin-1, neuropilin-2, plexin-A1 and integrin beta 1, wherein the transmembrane domain is fused to a heterologous sequence,
wherein the disease is selected from diseases associated with excessive angiogenesis and cancers.

2. The method of claim 1, wherein administration of the pharmaceutical composition releases a concentration of the peptidic antagonist of more than $10^{-12}$ M.

3. The method of claim 1, wherein the transmembrane domain has the amino acid sequence of the transmembrane domain of human neuropilin-1 as set forth in SEQ ID NO: 1, or of human neuropilin-2 as set forth in SEQ ID NO: 2, or of human plexin A1 as set forth in SEQ ID NO: 3 or of human integrin beta 1 as set forth in SEQ ID NO: 9.

4. The method according to claim 1, wherein the heterologous sequence allows at least one of: specific cellular location of the peptidic antagonist and improved purification yield of the peptidic antagonist.

* * * * *

SEQUENCE LISTING

<160> NUMBER OF SEQ ID NOS: 20

<210> SEQ ID NO 1
<211> LENGTH: 23
<212> TYPE: PRT
<213> ORGANISM: Artificial

```
<220> FEATURE:
<223> OTHER INFORMATION: Homo sapiens neuropilin-1 transmembrane domain

<400> SEQUENCE: 1

Ile Leu Ile Thr Ile Ile Ala Met Ser Ala Leu Gly Val Leu Leu Gly
1               5                   10                  15

Ala Val Cys Gly Val Val Leu
            20

<210> SEQ ID NO 2
<211> LENGTH: 25
<212> TYPE: PRT
<213> ORGANISM: Artificial
<220> FEATURE:
<223> OTHER INFORMATION: Homo sapiens neuropilin-2 transmembrane domain

<400> SEQUENCE: 2

Ile Leu Ile Thr Ile Ile Ala Met Ser Ser Leu Gly Val Leu Leu Gly
1               5                   10                  15

Ala Thr Cys Ala Gly Leu Leu Leu Tyr
            20                  25

<210> SEQ ID NO 3
<211> LENGTH: 27
<212> TYPE: PRT
<213> ORGANISM: Artificial
<220> FEATURE:
<223> OTHER INFORMATION: Homo sapiens plexin-A1 transmembrane domain

<400> SEQUENCE: 3

Leu Leu Thr Leu Pro Ala Ile Val Gly Ile Gly Gly Gly Gly Gly Leu
1               5                   10                  15

Leu Leu Leu Val Ile Val Ala Val Leu Ile Ala
            20                  25

<210> SEQ ID NO 4
<211> LENGTH: 28
<212> TYPE: PRT
<213> ORGANISM: Artificial
<220> FEATURE:
<223> OTHER INFORMATION: Mus musculus plexin-A2 transmembrane domain

<400> SEQUENCE: 4

Leu Leu Thr Leu Pro Ala Ile Ile Ser Ile Ala Ala Gly Gly Ser Leu
1               5                   10                  15

Leu Leu Ile Ile Val Ile Ile Val Leu Ile Ala Tyr
            20                  25

<210> SEQ ID NO 5
<211> LENGTH: 27
<212> TYPE: PRT
<213> ORGANISM: Artificial
<220> FEATURE:
<223> OTHER INFORMATION: Mus musculus plexin-A3 transmembrane domain

<400> SEQUENCE: 5

Leu Thr Leu Pro Ala Met Val Gly Leu Ala Ala Gly Gly Gly Leu Leu
1               5                   10                  15

Leu Leu Ala Ile Thr Val Val Leu Val Ala Tyr
            20                  25

<210> SEQ ID NO 6
<211> LENGTH: 26
<212> TYPE: PRT
```

```
<213> ORGANISM: Artificial
<220> FEATURE:
<223> OTHER INFORMATION: Homo sapiens plexin-A4 transmembrane domain

<400> SEQUENCE: 6

Leu Ser Leu Pro Ala Ile Val Ser Ile Ala Val Ala Gly Gly Leu Leu
1               5                   10                  15

Ile Ile Phe Ile Val Ala Val Leu Ile Ala
            20                  25

<210> SEQ ID NO 7
<211> LENGTH: 22
<212> TYPE: PRT
<213> ORGANISM: Artificial
<220> FEATURE:
<223> OTHER INFORMATION: Homo sapiens Nr-CAM transmembrane domain

<400> SEQUENCE: 7

Gly Trp Phe Ile Gly Leu Met Cys Ala Val Ala Leu Leu Ile Leu Ile
1               5                   10                  15

Leu Leu Ile Val Cys Phe
            20

<210> SEQ ID NO 8
<211> LENGTH: 23
<212> TYPE: PRT
<213> ORGANISM: Artificial
<220> FEATURE:
<223> OTHER INFORMATION: Mus musculus L1-CAM transmembrane domain

<400> SEQUENCE: 8

Gly Trp Phe Ile Ala Phe Val Ser Ala Ile Ile Leu Leu Leu Leu Ile
1               5                   10                  15

Leu Leu Ile Leu Cys Phe Ile
            20

<210> SEQ ID NO 9
<211> LENGTH: 23
<212> TYPE: PRT
<213> ORGANISM: Artificial
<220> FEATURE:
<223> OTHER INFORMATION: Homo sapiens integrin beta 1 transmembrane
      domain

<400> SEQUENCE: 9

Ile Ile Pro Ile Val Ala Gly Val Val Ala Gly Ile Val Leu Ile Gly
1               5                   10                  15

Leu Ala Leu Leu Leu Ile Trp
            20

<210> SEQ ID NO 10
<211> LENGTH: 23
<212> TYPE: PRT
<213> ORGANISM: Artificial
<220> FEATURE:
<223> OTHER INFORMATION: Mus musculus integrin beta 2 transmembrane
      domain

<400> SEQUENCE: 10

Val Ala Ala Ile Val Gly Gly Thr Val Val Gly Val Val Leu Ile Gly
1               5                   10                  15

Val Leu Leu Leu Val Ile Trp
            20
```

```
<210> SEQ ID NO 11
<211> LENGTH: 28
<212> TYPE: PRT
<213> ORGANISM: Artificial
<220> FEATURE:
<223> OTHER INFORMATION: Homo sapiens plexin-A2 transmembrane domain

<400> SEQUENCE: 11

Leu Leu Thr Leu Pro Ala Ile Val Ser Ile Ala Ala Gly Gly Ser Leu
1               5                   10                  15

Leu Leu Ile Ile Val Ile Ile Val Leu Ile Ala Tyr
            20                  25

<210> SEQ ID NO 12
<211> LENGTH: 26
<212> TYPE: PRT
<213> ORGANISM: Artificial
<220> FEATURE:
<223> OTHER INFORMATION: Homo sapiens plexin-A3 transmembrane domain

<400> SEQUENCE: 12

Leu Thr Leu Pro Ala Met Met Gly Leu Ala Ala Gly Gly Gly Leu Leu
1               5                   10                  15

Leu Leu Ala Ile Thr Ala Val Leu Val Ala
            20                  25

<210> SEQ ID NO 13
<211> LENGTH: 20
<212> TYPE: PRT
<213> ORGANISM: Artificial
<220> FEATURE:
<223> OTHER INFORMATION: Homo sapiens L1-CAM transmembrane domain

<400> SEQUENCE: 13

Gly Trp Phe Ile Gly Phe Val Ser Ala Ile Ile Leu Leu Leu Leu Val
1               5                   10                  15

Leu Leu Ile Leu
            20

<210> SEQ ID NO 14
<211> LENGTH: 23
<212> TYPE: PRT
<213> ORGANISM: Artificial
<220> FEATURE:
<223> OTHER INFORMATION: Homo sapiens integrin beta 2 transmembrane
      domain

<400> SEQUENCE: 14

Ile Ala Ala Ile Val Gly Gly Thr Val Ala Gly Ile Val Leu Ile Gly
1               5                   10                  15

Ile Leu Leu Leu Val Ile Trp
            20

<210> SEQ ID NO 15
<211> LENGTH: 23
<212> TYPE: PRT
<213> ORGANISM: Artificial
<220> FEATURE:
<223> OTHER INFORMATION: Gallus gallus neuropilin-1 transmembrane domain

<400> SEQUENCE: 15

Ile Leu Ile Thr Ile Ile Ala Met Ser Ala Leu Gly Val Leu Leu Gly
1               5                   10                  15

Ala Ile Cys Gly Val Val Leu
            20
```

```
<210> SEQ ID NO 16
<211> LENGTH: 23
<212> TYPE: PRT
<213> ORGANISM: Artificial
<220> FEATURE:
<223> OTHER INFORMATION: Zebrafish neuropilin-1 transmembrane domain

<400> SEQUENCE: 16

Ile Leu Ile Thr Ile Ile Ala Met Ser Ala Leu Gly Val Phe Leu Gly
1               5                   10                  15

Ala Ile Cys Gly Val Val Leu
            20

<210> SEQ ID NO 17
<211> LENGTH: 25
<212> TYPE: PRT
<213> ORGANISM: Artificial
<220> FEATURE:
<223> OTHER INFORMATION: Gallus gallus neuropilin-2 transmembrane domain

<400> SEQUENCE: 17

Ile Leu Val Thr Ile Ile Ala Met Ser Ser Leu Gly Val Leu Leu Gly
1               5                   10                  15

Ala Thr Cys Ala Gly Leu Leu Leu Tyr
            20                  25

<210> SEQ ID NO 18
<211> LENGTH: 24
<212> TYPE: PRT
<213> ORGANISM: Artificial
<220> FEATURE:
<223> OTHER INFORMATION: EGFR transmembrane domain

<400> SEQUENCE: 18

Ser Ile Ala Thr Gly Met Val Gly Ala Leu Leu Leu Leu Leu Val Val
1               5                   10                  15

Ala Leu Gly Ile Gly Leu Phe Met
            20

<210> SEQ ID NO 19
<211> LENGTH: 23
<212> TYPE: PRT
<213> ORGANISM: Artificial
<220> FEATURE:
<223> OTHER INFORMATION: ERB-2 transmembrane domain

<400> SEQUENCE: 19

Ser Ile Ile Ser Ala Val Val Gly Ile Leu Leu Val Val Val Leu Gly
1               5                   10                  15

Val Val Phe Gly Ile Leu Ile
            20

<210> SEQ ID NO 20
<211> LENGTH: 23
<212> TYPE: PRT
<213> ORGANISM: Artificial
<220> FEATURE:
<223> OTHER INFORMATION: Glycophorine A transmembrane domain

<400> SEQUENCE: 20

Ile Thr Leu Ile Ile Phe Gly Val Met Ala Gly Val Ile Gly Thr Ile
1               5                   10                  15
```

```
Leu Leu Ile Ser Tyr Gly Ile
            20
```